United States Patent
Al-Abed et al.

(10) Patent No.: US 9,440,914 B2
(45) Date of Patent: Sep. 13, 2016

(54) METHOD FOR TREATING GLIOBLASTOMAS AND OTHER TUMORS

(71) Applicant: THE FEINSTEIN INSTITUTE FOR MEDICAL RESEARCH, Manhasseet, NY (US)

(72) Inventors: Yousef Al-Abed, Dix Hills, NY (US); Marc Symons, Roslyn Estates, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 14/211,998

(22) Filed: Mar. 14, 2014

(65) Prior Publication Data
US 2014/0323576 A1   Oct. 30, 2014

Related U.S. Application Data

(60) Provisional application No. 61/793,207, filed on Mar. 15, 2013.

(51) Int. Cl.
*A61K 31/167*   (2006.01)
*C07C 279/00*   (2006.01)
*A61K 45/06*   (2006.01)

(52) U.S. Cl.
CPC ........... *C07C 279/00* (2013.01); *A61K 31/167* (2013.01); *A61K 45/06* (2013.01)

(58) Field of Classification Search
CPC .. C07C 279/00; C07C 279/02; A61K 31/167
See application file for complete search history.

(56) References Cited

U.S. PATENT DOCUMENTS

2011/0201686 A1   8/2011   Al-Abed

OTHER PUBLICATIONS

WebMd. Brain Center and Health. (2014) 1-3. < http://www.webmd.com/cancer/brain-cancer/what-is-astrocytoma>.*
Bruce, Jeffrey. Medscape: Glioblastoma Multiforme Treatment & Management. (2014) 1-8.*
Bianchi, Marina. Molecular Medicine, 1:3. (1995) 254-266.*
Miller I S et al, entitled "Pharmacological inhibition of microglia leads to increased survival in a murine model of glioblastoma multiforme in conjunction with ionizing radiation," Presentation, Apr. 4, 2012, Abstract Only.
Erin N et al., entitled "Activation of vagus nerve by semapimod alters substance P levels and decreases breask cancer metastasis," Regulatory Peptides, 179, 2012, pp. 101-108.

* cited by examiner

*Primary Examiner* — Golam M M Shameem
*Assistant Examiner* — Laura Daniel
(74) *Attorney, Agent, or Firm* — Amster, Rothstein & Ebenstein LLP

(57) ABSTRACT

Methods of treating an astrocytoma with agents effective to inhibit microglia function are provided, as well as methods of enhancing the efficacy of brain tumor radiation therapy on an astrocytoma in a subject. Also provided are methods of treating other solid tumor types, and tumor cell invasion, with guanylhydrazone compounds.

9 Claims, 12 Drawing Sheets

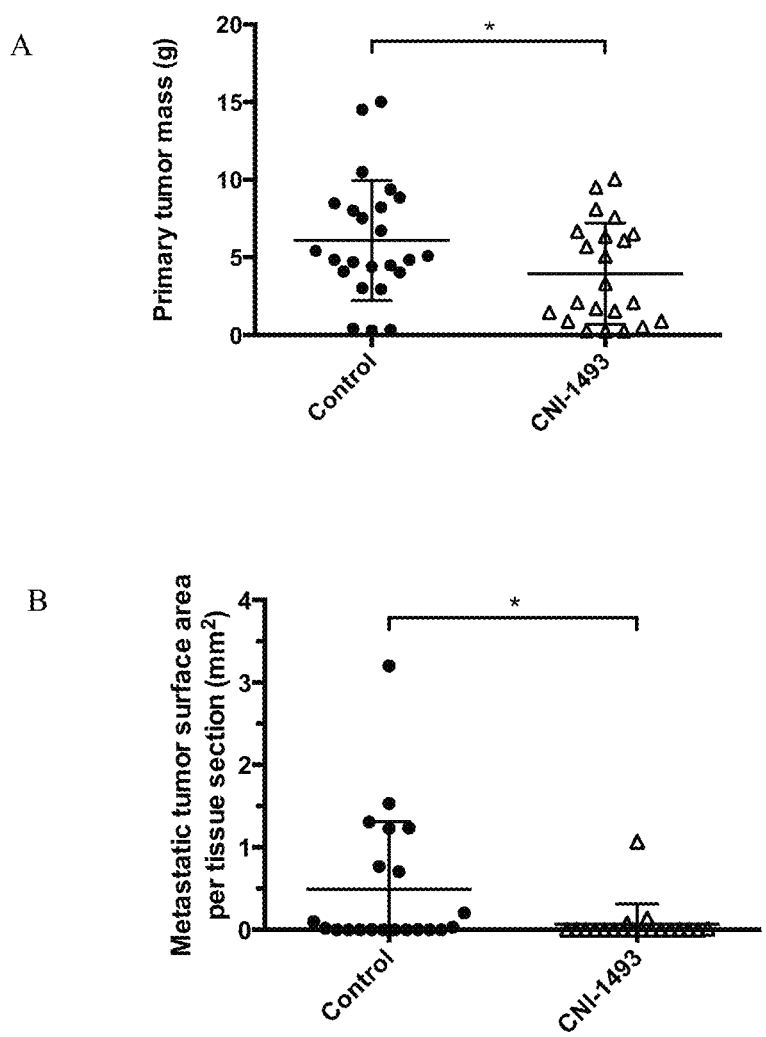
Fig. 8A-B a) 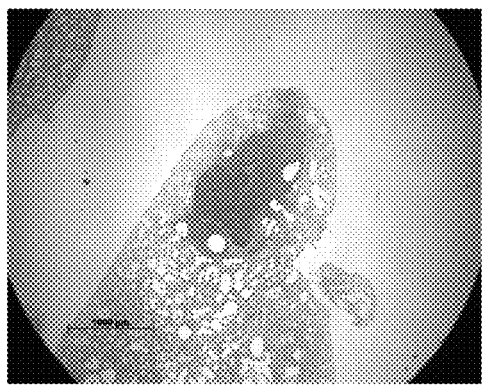 b) 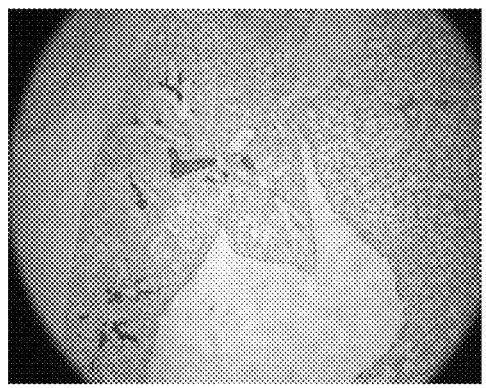
Fig. 9A-B

METHOD FOR TREATING GLIOBLASTOMAS AND OTHER TUMORS

CROSS-REFERENCE TO RELATED APPLICATIONS

This application claims benefit of U.S. Provisional Application No. 61/793,207, filed Mar. 15, 2013, the contents of which are hereby incorporated by reference.

BACKGROUND OF THE INVENTION

Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Glioblastoma Multiforme (GBM) is the most malignant and lethal form of astrocytoma (WHO grade IV). Despite recent advancements in the standards of care, the outlook for GBM patients remains bleak and new therapies are therefore swiftly required. Currently, the standard of care is gross tumor resection followed by radiation treatment and concurrent chemotherapy. However, even after extensive therapy, relapse is certain and the disease remains lethal (1).

Microglia are the resident macrophages of the central nervous system (CNS) (2, 3). They are glial cells that are of hematopoietic origin. Microglia are the main phagocytic and immunocompetent cells in the CNS. They are activated by damage or infection and phagocytose debris and other cells. They also present antigens and secrete cytokines that regulate inflammatory responses. Microglia are attracted by glial tumors via multiple tumor-secreted factors and are enriched in the tumor periphery (4, 5). The extent of microglia infiltration correlates with tumor grade (6, 7). In glioblastoma, microglia account for as much as 30% of the tumor mass (8). Instead of producing an anti-tumor effect, microglia are co-opted by the tumor to favor its growth (4, 5). In this reprogrammed state, they support the tumor by secreting factors that promote immunosuppression, and glioblastoma cell proliferation, invasion and angiogenesis. Importantly, selective ablation of microglia has been shown to inhibit glioblastoma invasiveness and growth (9, 10).

Additionally, solid tumors in general are also a challenge to treat with non-surgical means. Additionally, solid tumors in general are also a challenge to treat with non-surgical means. Novel methods to treat solid tumors are urgently needed. Importantly, macrophages are thought to be necessary for the malignant behavior of many, if not most, solid tumors, including Ewing's sarcoma (De Palma M, Lewis C E: Macrophage regulation of tumor responses to anticancer therapies. Cancer Cell. 2013, 23:277-286/Fujiwara T et al: Macrophage Infiltration Predicts a Poor Prognosis for Human Ewing Sarcoma. Am J Pathol 2011, 179:1157-1170).

The present invention addresses the need for improved astrocytoma treatments, including for glioblastomas, and new methods for treating solid tumors, including Ewing's sarcoma.

SUMMARY OF THE INVENTION

A method of treating a solid tumor in a subject is provided comprising administering to the subject an amount of a guanylhydrazone compound effective to treat a solid tumor in a subject.

Also provided is a method of treating an astrocytoma in a subject comprising administering to the subject an amount of an agent that inhibits microglia function effective to treat an astrocytoma.

Also provided is a method of enhancing the efficacy of radiation therapy on an astrocytoma in a subject comprising administering to the subject an amount of an agent which inhibits microglial function effective to enhance the efficacy of brain tumor radiation.

An agent is provided for treating an astrocytoma in a subject, or for enhancing the efficacy of radiation therapy on an astrocytoma in a subject having the astrocytoma, or for treating a solid tumor in a subject, the agent comprising a compound having the formula:

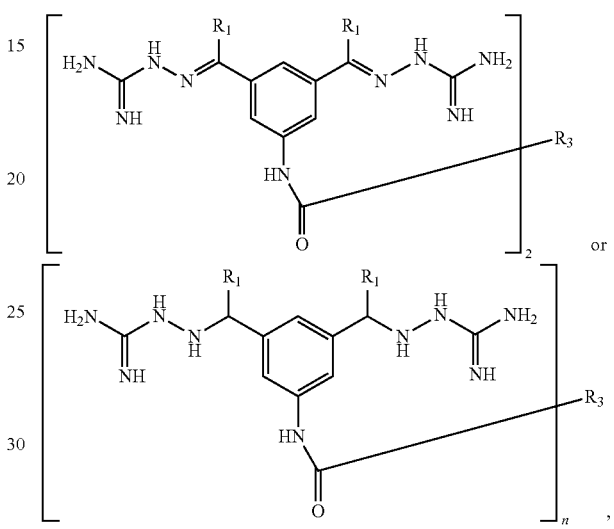

wherein in each case, n=1 or 2, and wherein when n=2 the two molecules are joined through $R_3$, wherein each $R_1$ is, independently, chosen from —H or —$CH_3$, and wherein $R_3$ is a C1-C10 hydrocarbyl, branched or unbranched, optionally substituted;

or comprising a compound having the formula:

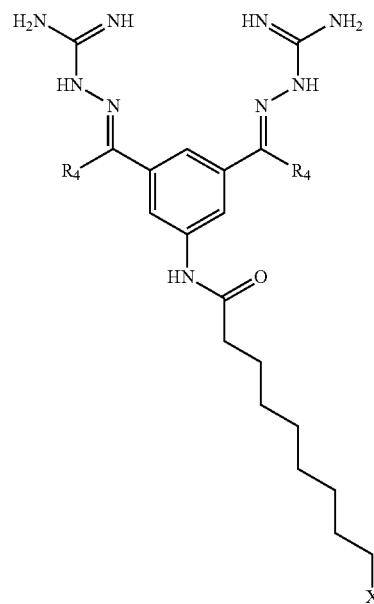

wherein each $R_4$ is, independently, chosen from —H or —CH$_3$,
and wherein X=C2-C8 alkynyl, —CN$_3$, or —C(O)NHR wherein R is a di-substituted aryl, or is a pharmaceutically acceptable salt thereof.

Also provided is a method of preventing or inhibiting metastasis of a solid tumor in a subject comprising administering to the subject an amount of a guanylhydrazone compound effective to prevent or inhibit metastasis of a solid tumor in a subject.

BRIEF DESCRIPTION OF THE DRAWINGS

FIG. 8A-8B. CNI-1493 decreases primary tumor size and metastatic burden in a metastatic Ewing's Sarcoma mouse model. $10^6$ SK-ENP1 cells were implanted into the kidneys of nude mice and intraperitoneal treatment with CNI-1493 (5 mg/kg/day) or vehicle was initiated one week later. After six weeks of treatment, mice were sacrificed and assessed for primary and metastatic tumor burden. Primary tumor mass was significantly less in CNI-1493-treated mice (A). Metastatic tumor burden was evaluated with hematoxylin and eosin stained tissue sections by microscopy and calculating surface area per tissue section per mouse using ImageJ software (B). CNI-1493-treated mice had significantly less metastatic disease burden. *p<0.05, error bars represent standard deviation.

FIG. 9A-9B. Representative lung sections of mice with metastatic disease. Control mice had larger metastases invading lung parenchyma (A), whereas CNI-1493-treated mice had smaller metastatic tumors that remained within the vasculature (B).

DETAILED DESCRIPTION OF THE INVENTION

Figures 1A, 1B, 1C:
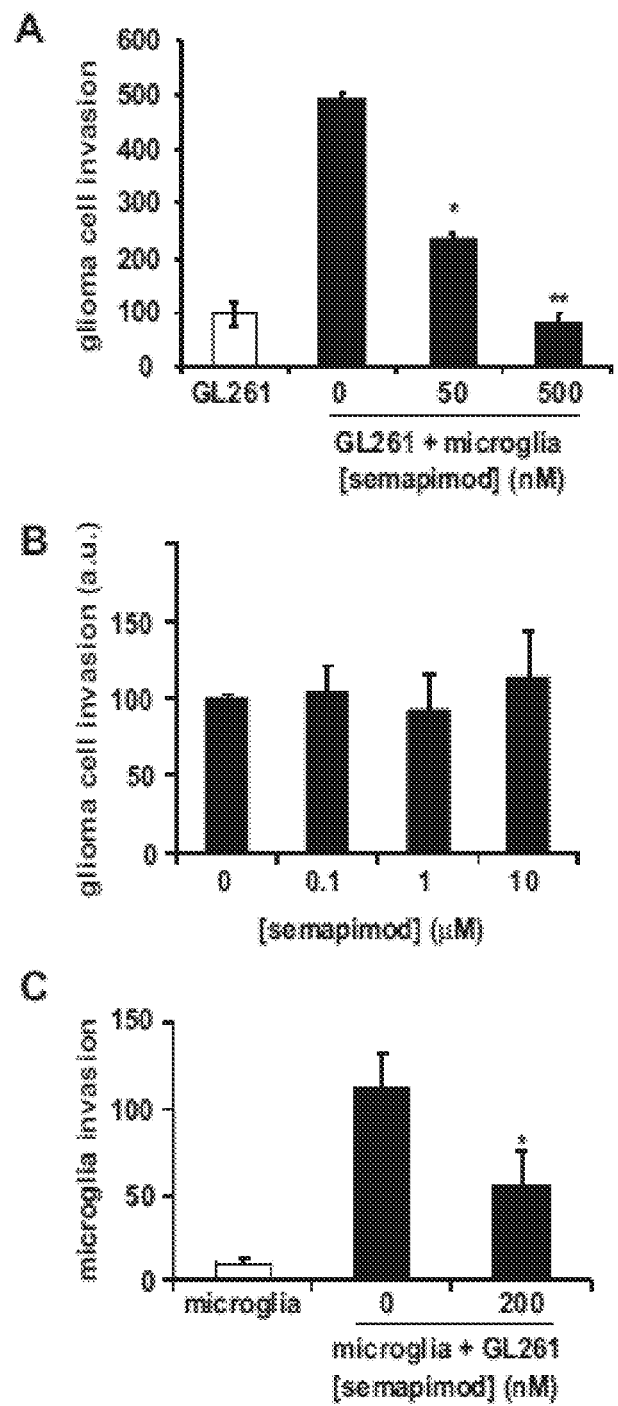
FIG. 1A-1C. Semapimod inhibits microglia-stimulated glioblastoma invasion in vitro. (A) Semapimod inhibits microglia-stimulated glioblastoma cell invasion. GL261 cells were embedded in basement membrane extract (BME) with or without microglia in the presence of the indicated concentrations of semapimod, layered in the transwell and incubated for 48 h. The number of invading GL261 cells was determined. Data shown represent the average+/−SEM of 3 independent experiments, performed in duplicate. (B) Semapimod does not affect serum-stimulated glioblastoma cell invasion. GL261 cells embedded in BME in the presence of the indicated concentration of semapimod, were layered in the transwell and incubated for 48 h. Serum (10% FBS) was added to the bottom well. The number of invading GL261 cells was determined. Data shown represent the average+/−SEM of 3 independent experiments. (C) Semapimod inhibits glioblastoma cell-stimulated microglia invasion. Glioblastoma cells were plated in the bottom well and microglia were embedded in BME in the presence or absence of 200 nM semapimod, layered in the transwell and incubated for 48 h. Data shown represent the average+/−SEM of 3 independent experiments. *: p<0.05, **: p<0.01 student's 2 tailed t-test.

A method of treating a solid tumor in a subject is provided comprising administering to the subject an amount of a guanylhydrazone compound effective to treat a solid tumor in a subject.

In an embodiment, the solid tumor is a brain tumor, a breast tumor, a sarcoma, or a tumor of the nasopharynx, pharynx, lung, bone, brain, sialaden, stomach, esophagus, testes, ovary, uterus, endometrium, liver, small intestine, appendix, colon, rectum, bladder, gall bladder, pancreas, kidney, urinary bladder, breast, cervix, vagina, vulva, prostate, thyroid, skin, head or neck, or is a glioma. In an embodiment the solid tumor is a breast tumor, a sarcoma or an astrocytoma. In an embodiment, the tumor is brain tumor. In an embodiment, the brain tumor is an astrocytoma. In an embodiment, the tumor is a breast tumor. In an embodiment, the tumor is a sarcoma. In an embodiment, the sarcoma is Ewing's sarcoma. In an embodiment, the tumor is cancerous. In an embodiment, the tumor is an invasive tumor. In a preferred embodiment, the tumor is a primary tumor. In an embodiment, the tumor has not metastasized in the subject. In an embodiment, the tumor is not suspected of metastasizing and/or the subject has not or is no being treated for metastasis. In an embodiment, the treatment reduces the size of the tumor. In an embodiment, the treatment inhibits further growth of the tumor. In an embodiment, the treatment inhibits invasion by cells of the tumor.

Guanylhydrazones are known in the art, for example see Bianchi et al. An inhibitor of macrophage arginine transport and nitric oxide production (CNI-1493) prevents acute inflammation and endotoxin lethality. *Molecular Medicine* (Baltimore, Md., United States) (1995), 1(3), 254-66; U.S. Pat. Nos. 6,248,787; 6,180,676; 6,022,900; 6,008,255; 5,859,062; 5,854,289; 5,849,794; 5,753,684; 5,750,573; and 5,599,984 all to Bianchi et al; and U.S. Pat. No. 7,863,334, Sielecki-Dzurdz, each of which are hereby incorporated by reference in their entirety.

In an embodiment of the methods, the guanylhydrazone compound has the following structure:

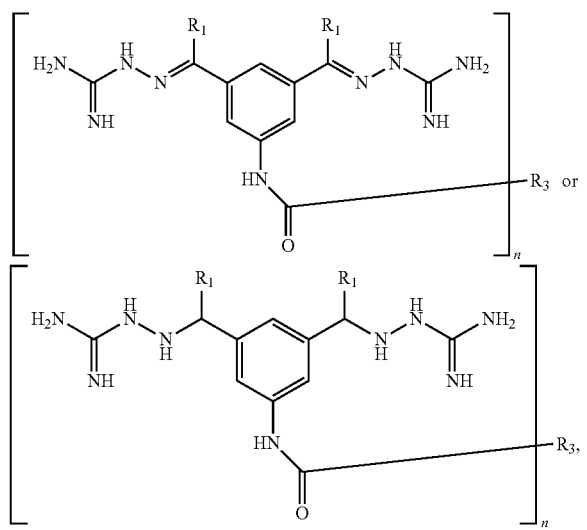

wherein, in each case, n=1 or 2, and wherein when n=2, the two molecules are joined through R$_3$, wherein each R$_1$ is, independently, chosen from —H or —CH$_3$, and wherein R$_3$ is a C1-C10 hydrocarbyl, branched or unbranched, optionally substituted; or the guanylhydrazone compound has the following structure:

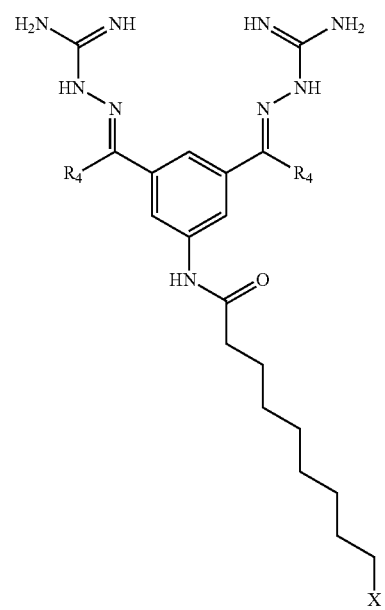

wherein each R$_4$ is, independently, chosen from —H or —CH$_3$, and wherein X=C2-C8 alkynyl, —CN$_3$, or —C(O)NHR wherein R is a di-substituted aryl, or is a pharmaceutically acceptable salt thereof.

In an embodiment, the guanylhydrazone compound comprises a compound having the structure:

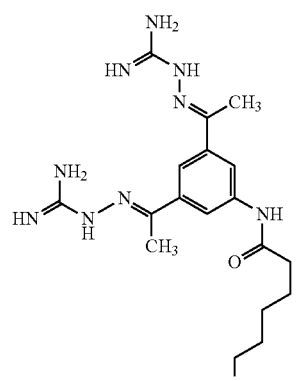

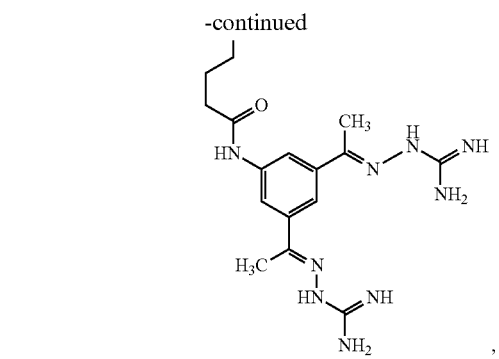

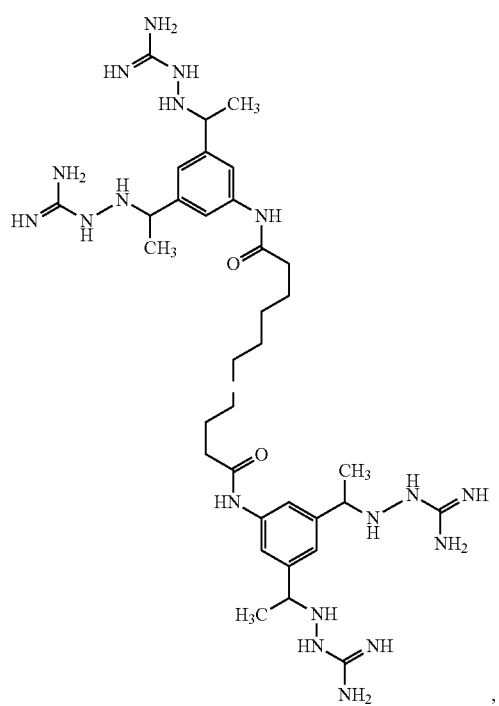

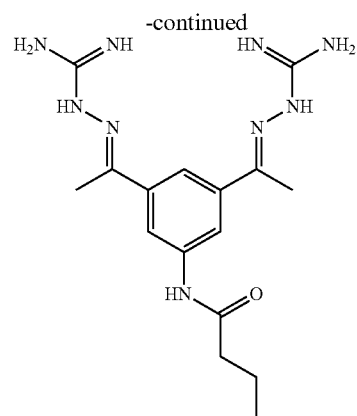

or is a pharmaceutically acceptable salt thereof.

In an embodiment, the compound is administered systemically. In an embodiment, the compound is administered directly onto or into the tumor.

In an embodiment, the method further comprises treating the subject with a chemotherapy and/or a radiotherapy effective to treat a solid tumor in a subject.

Also provided is a method of treating an astrocytoma in a subject comprising administering to the subject an amount of an agent that inhibits microglia function effective to treat an astrocytoma.

In an embodiment, the subject is also being treated with ionizing radiotherapy for the astrocytoma.

In an embodiment, the astrocytoma is a glioblastoma. In an embodiment, the glioblastoma is a glioblastoma multiforme. In an embodiment, the agent comprises a guanylhydrazone.

In an embodiment, the agent comprises a compound having the formula:

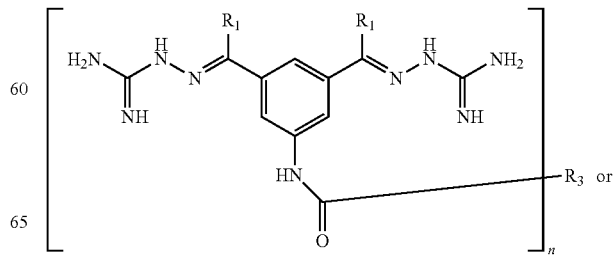

-continued

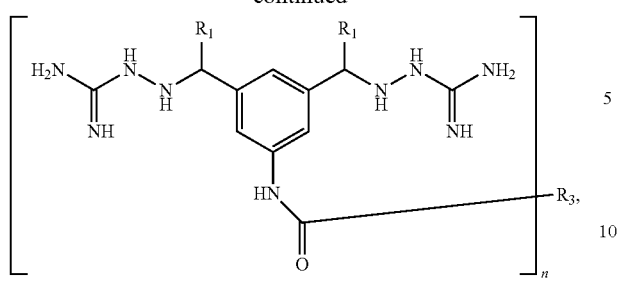

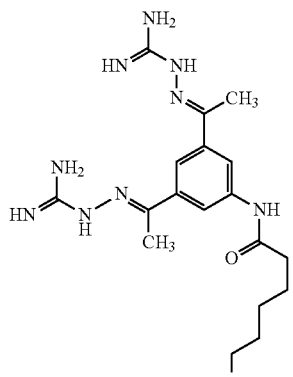

wherein in each case, n=1 or 2, and wherein when n=2, the two molecules are joined through R₃, wherein each $R_1$ is, independently, chosen from —H or —CH₃, and wherein $R_3$ is a C1-C10 hydrocarbyl, branched or unbranched, optionally substituted;

or wherein the agent comprises a compound having the formula:

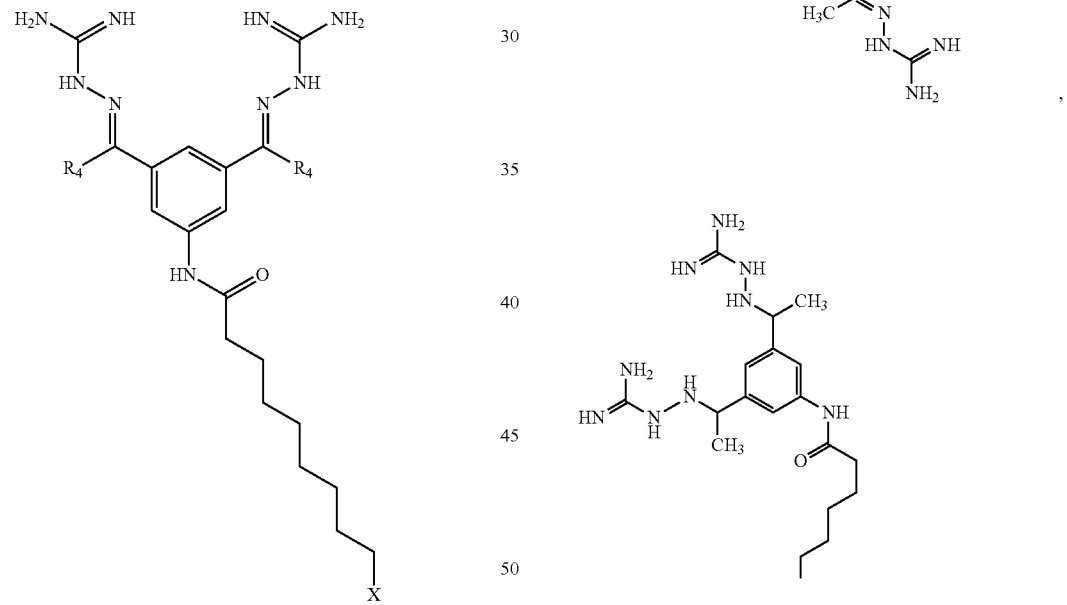

wherein each $R_4$ is, independently, chosen from —H or —CH₃, and wherein X=C2-C8 alkynyl, —CN₃, or —C(O)NHR wherein R is a di-substituted aryl, or is a pharmaceutically acceptable salt thereof. In an embodiment, $R_3$ is a C1, C2, C3, C4, C5, C6, C7, C8, C9 or C10 hydrocarbyl. In an embodiment, $R_3$ is a C8 hydrocarbyl.

In an embodiment, the agent comprises a compound having the structure:

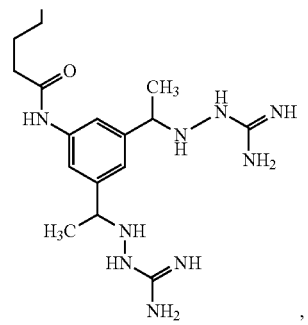

-continued

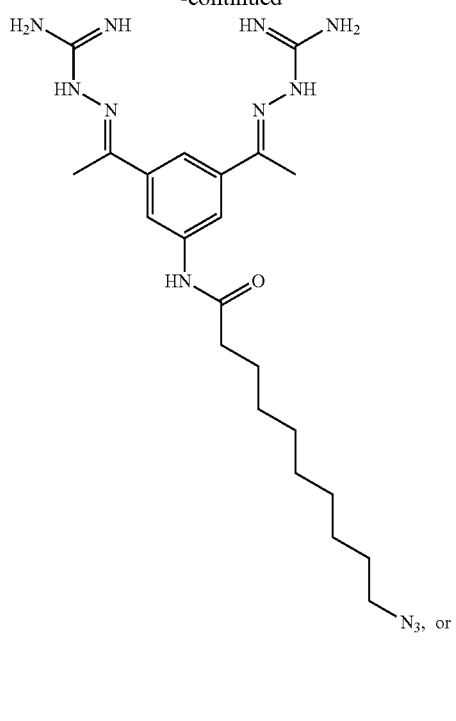

N₃, or

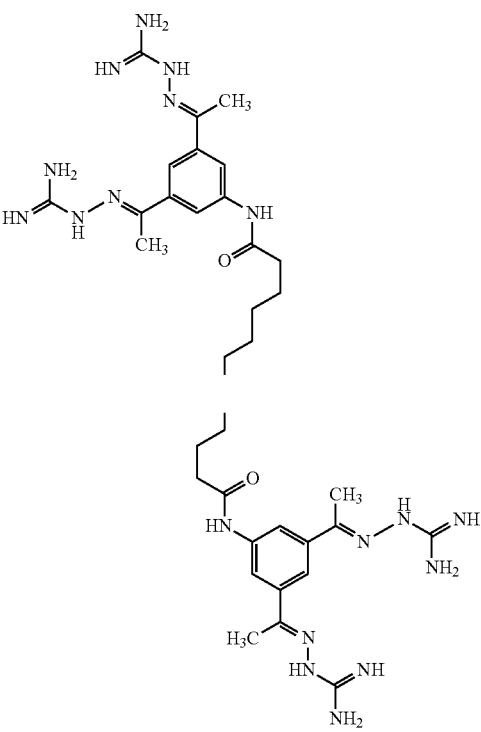

or is a pharmaceutically acceptable salt thereof.

In an embodiment, the agent comprises a compound having the structure:

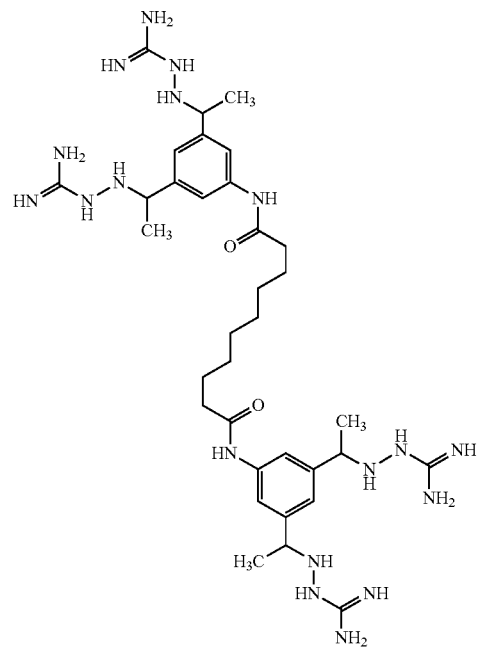 [SMILES: CC(NNC(=N)N)c1cc(NC(=O)CCCCCCCCC(=O)Nc2cc(C(C)NNC(=N)N)cc(C(C)NNC(=N)N)c2)cc(C(C)NNC(=N)N)c1]

or is a pharmaceutically acceptable salt thereof.

In an embodiment, the agent is administered in a manner effective to deliver it to a brain of a subject. In an embodiment, the agent is administered directly into the brain of the subject.

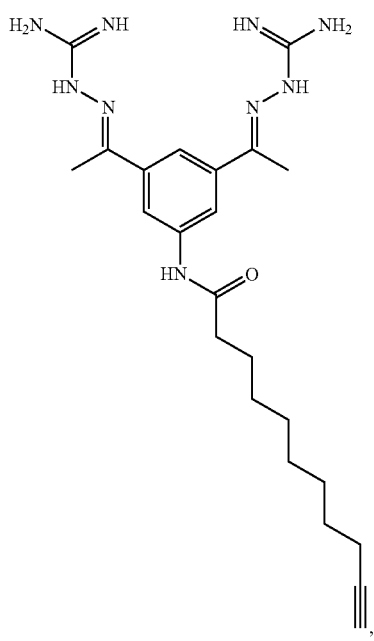

or is a pharmaceutically acceptable salt thereof.

In an embodiment, the agent comprises a compound having the structure:

In an embodiment, the subject does not have a neurodegenerative disease or is not known to have neurodegenerative disease and/or has not been diagnosed with a neurodegenerative disease.

In an embodiment, the subject does not have an inflammatory disease or is not known to have an inflammatory disease and/or has not been diagnosed with an inflammatory disease.

In an embodiment, the method further comprises administering an anti-tumor therapy to the subject.

In an embodiment, the anti-tumor therapy comprises brain tumor radiation therapy. In an embodiment, the dose of brain tumor radiation therapy is 1-60 Gy. In an embodiment, the dose of brain tumor radiation therapy is 20-60 Gy. In an embodiment, the dose of brain tumor radiation therapy is 30-60 Gy. The brain tumor radiation therapy can be administered before, during or after the administration of the agent that inhibits microglia function. In a preferred embodiment, the brain tumor radiation therapy is administered while the agent that inhibits microglia function is still present in the subject. In an embodiment the brain tumor radiation therapy is administered in fractions. In an embodiment the brain tumor radiation therapy is administered in fractions of 1-3 Gy.

In an embodiment, the anti-tumor therapy comprises anti-tumor chemotherapy. In an embodiment, the method comprises administering a DNA alkylating and/or DNA methylating chemotherapy to the subject. In an embodiment, the DNA alkylating and/or DNA methylating chemotherapy comprises temozolomide.

In an embodiment, the method further comprises administering an angiogenesis-inhibiting agent to the subject. In an embodiment, the angiogenesis-inhibiting agent comprises an anti-vascular endothelial growth factor A (VEGF-A) antibody or a VEGF-A-binding fragment of such an antibody. In an embodiment, the angiogenesis-inhibiting agent is bevacizumab.

Also provided is a method of enhancing the efficacy of brain tumor radiation therapy on an astrocytoma in a subject comprising administering to the subject an amount of an agent which inhibits microglial function effective to enhance the efficacy of brain tumor radiation.

In an embodiment, the astrocytoma is a glioblastoma. In an embodiment, the glioblastoma is a glioblastoma multiforme. In an embodiment, the agent comprises a guanylhydrazone. Human astrocytomas are graded by the WHO into four grades: I, II, III and IV. The invention encompasses treatment of any one of these grades. In an embodiment, the astrocytoma is a glioblastoma. In a preferred embodiment, a glioblastoma multiforme. In an embodiment of the method, the subject is also being treated with ionizing radiotherapy for the astrocytoma. Radiotherapy is a well-established treatment technique for astrocytomas.

In an embodiment, the agent is administered in a manner effective to deliver it to a brain of a subject. In an embodiment, the agent is administered into the brain of the subject. Methods for such delivery are known in the art, such as direct cannulation, catheter (including microcatheter), injection, spray, by nanocarriers. Administration after or with an agent that increases permeability of the blood-brain barrier, such as mannitol, is also encompassed.

In an embodiment, the agent comprises a compound having the formula:

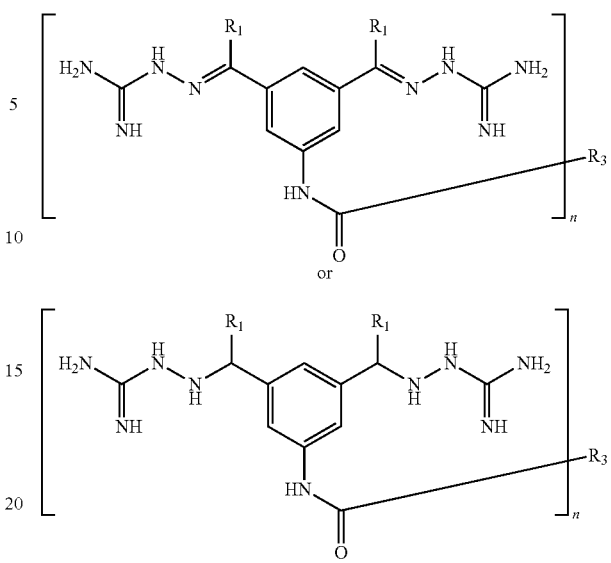

wherein in each case, n=1 or 2, and wherein when n=2 the two molecules are joined through $R_3$, wherein each $R_1$ is, independently, chosen from —H or —$CH_3$, and wherein $R_3$ is a C1-C10 hydrocarbyl, branched or unbranched, optionally substituted;

or the agent comprises a compound having the formula:

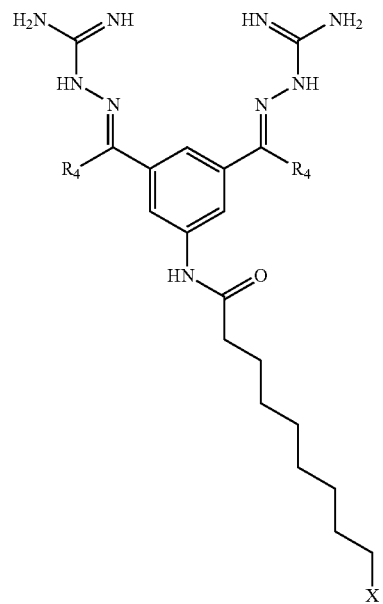

wherein each $R_4$ is, independently, chosen from —H or —$CH_3$, and wherein X=C2-C8 alkynyl, —$CN_3$, or —C(O)NHR wherein R is a di-substituted aryl, or is a pharmaceutically acceptable salt thereof. In an embodiment, $R_3$ is a C1, C2, C3, C4, C5, C6, C7, C8, C9 or C10 hydrocarbyl. In an embodiment, $R_3$ is a C8 hydrocarbyl.

In an embodiment, the agent comprises a compound having the structure:

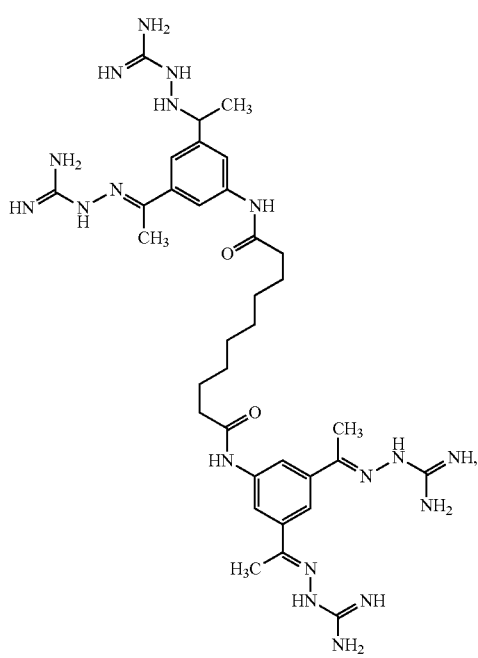
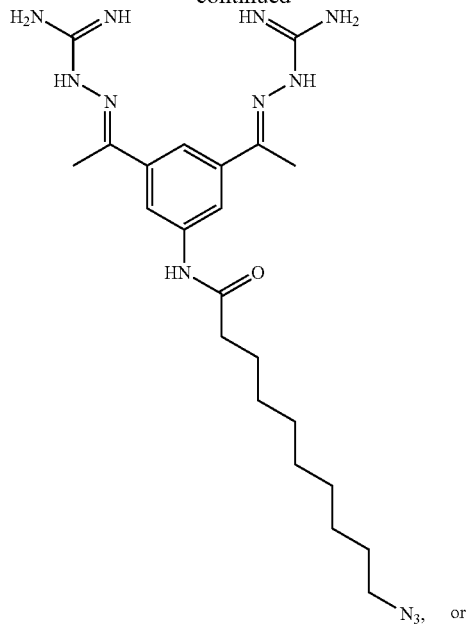
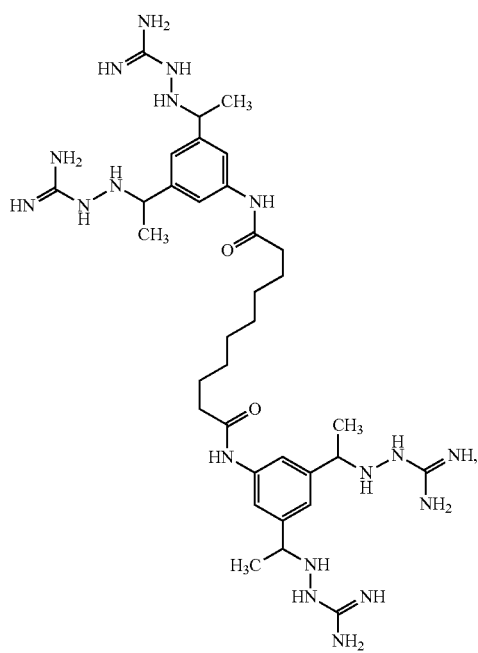
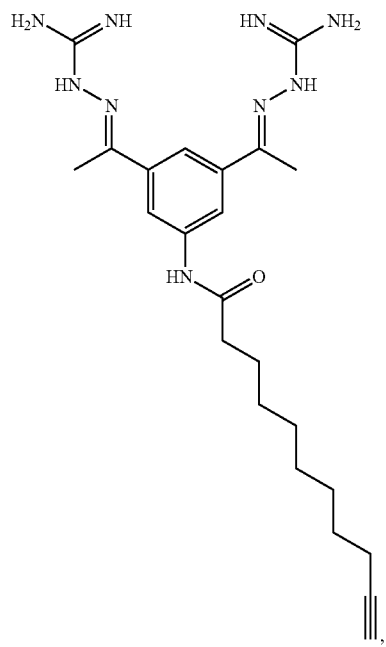
or is a pharmaceutically acceptable salt thereof.
In an embodiment, the agent comprises a compound having the structure:

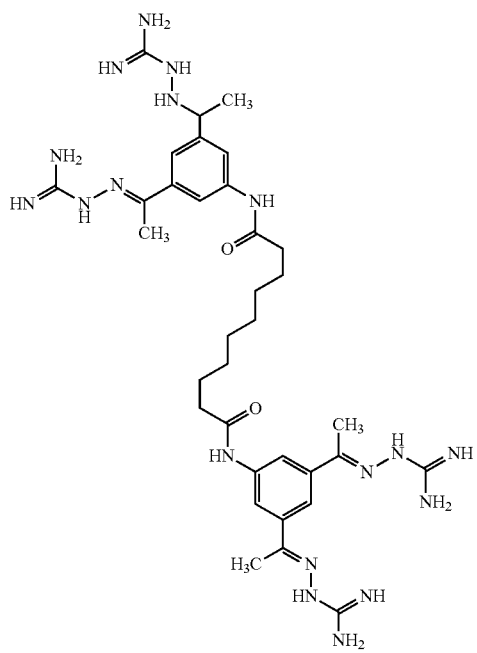 [SMILES: C/C(=N\NC(=N)N)c1cc(NC(=O)CCCCCCCCC(=O)Nc2cc(/C(C)=N/NC(=N)N)cc(C(C)NNC(=N)N)c2)cc(/C(C)=N/NC(=N)N)c1]

or is a pharmaceutically acceptable salt thereof.

In an embodiment, the agent is administered in a manner effective to deliver it to a brain of a subject. In an embodiment, agent is administered into the brain of the subject. In an embodiment, the subject does not have a neurodegenerative disease or is not known to have neurodegenerative disease and/or has not been diagnosed with a neurodegenerative disease. In an embodiment, the subject does not have an inflammatory disease or is not known to have an inflammatory disease and/or has not been diagnosed with an inflammatory disease.

In an embodiment, the method further comprises administering an additional anti-tumor therapy to the subject. In an embodiment, the anti-tumor therapy is a chemotherapy.

In an embodiment, the method further comprises administering an DNA alkylating and/or DNA methylating chemotherapy to the subject. In an embodiment, the DNA alkylating and/or DNA methylating chemotherapy comprises temozolomide.

In an embodiment, the method further comprises administering an angiogenesis-inhibiting agent to the subject. In an embodiment, the angiogenesis-inhibiting agent comprises an anti-vascular endothelial growth factor A (VEGF-A) antibody or a VEGF-A-binding fragment of such an antibody. In an embodiment, the angiogenesis-inhibiting agent is bevacizumab.

In a preferred embodiment, of the methods described herein, the subject is a human.

A composition is provided comprising a pharmaceutically acceptable carrier and an agent for treating an astrocytoma in a subject, or for enhancing the efficacy of brain tumor radiation therapy on an astrocytoma in a subject having the astrocytoma, or for treating a solid tumor in a subject, the agent comprising a compound having the formula:

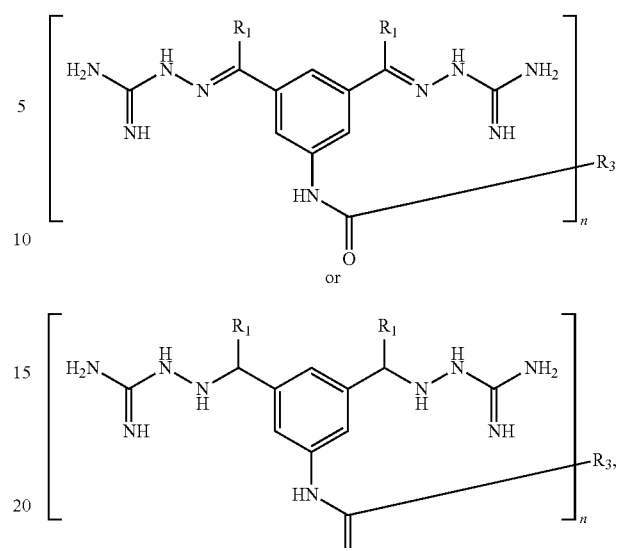

wherein in each case, n=1 or 2, and wherein when n=2 the two molecules are joined through $R_3$, wherein each $R_1$ is, independently, chosen from —H or —$CH_3$, and wherein $R_3$ is a C1-C10 hydrocarbyl, branched or unbranched, optionally substituted;

or comprising a compound having the formula:

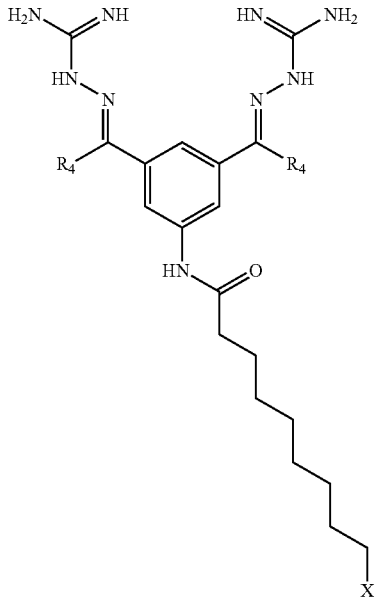

wherein each $R_4$ is, independently, chosen from —H or —$CH_3$, and wherein X=C2-C8 alkynyl, —$CN_3$, or —C(O)NHR wherein R is a di-substituted aryl, or a pharmaceutically acceptable salt thereof. In an embodiment, $R_3$ is a C1, C2, C3, C4, C5, C6, C7, C8, C9 or C10 hydrocarbyl. In an embodiment, $R_3$ is a C8 hydrocarbyl.

In an embodiment, the agent comprises a compound having the structure:

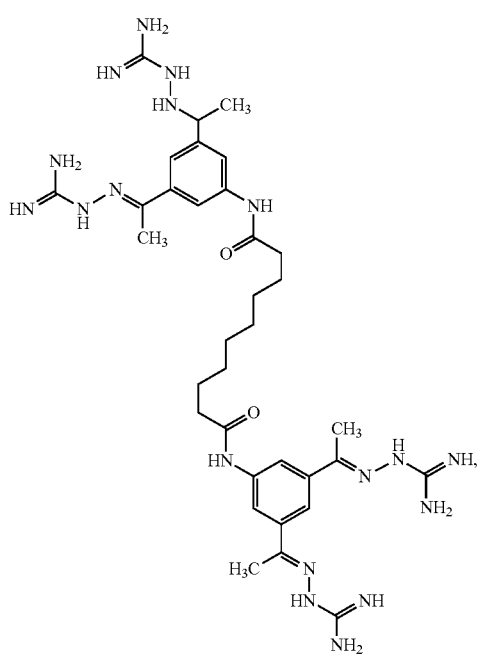

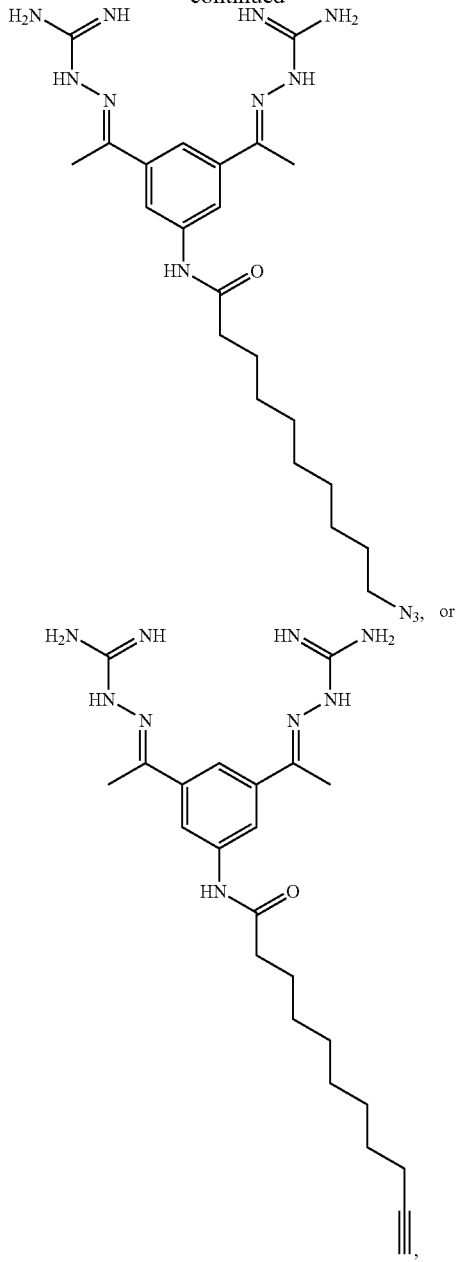

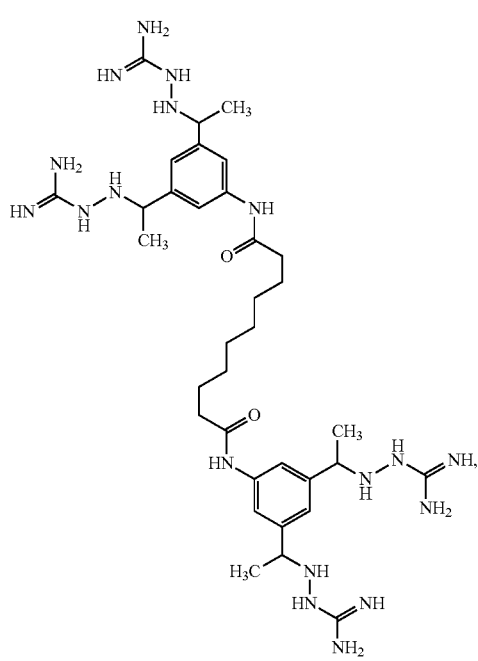

or is a pharmaceutically acceptable salt thereof.

Also provided is a method of preventing or inhibiting metastasis of a solid tumor in a subject comprising administering to the subject an amount of a guanylhydrazone compound effective to prevent or inhibit metastasis of a solid tumor in a subject.

In an embodiment, the solid tumor is a sarcoma, nephroblastoma or neuroblastoma. In an embodiment, the sarcoma is a Ewing's sarcoma. In an embodiment, the sarcoma is an osteosarcoma. In an embodiment, the sarcoma is a rhabdomyosarcoma. In an embodiment, the sarcoma is a low, medium or high grade unspecified sarcoma. In an embodiment, the nephroblastoma is a Wilms tumor. In an embodiment, the nephroblastoma is a rhabdoid tumor. In an embodiment, the method further comprises treating the subject with a chemotherapy and/or a radiotherapy effective to prevent or inhibit metastasis of a solid tumor in a subject. In an embodiment, the guanylhydrazone compound has the following structure:

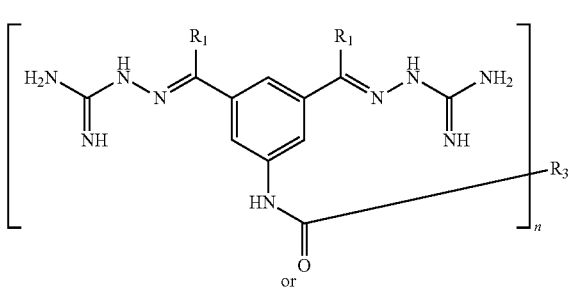

or

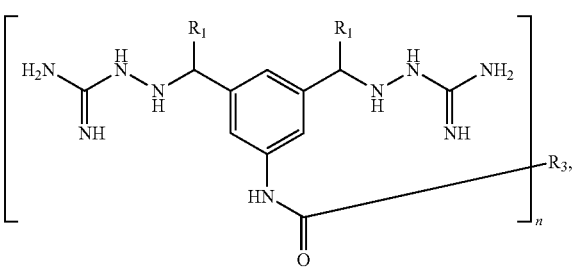

wherein, in each case, n=1 or 2, and wherein when n=2, the two molecules are joined through $R_3$, wherein each $R_1$ is, independently, chosen from —H or —CH$_3$, and wherein $R_3$ is a C1-C10 hydrocarbyl, branched or unbranched, optionally substituted;

or wherein the guanylhydrazone compound has the following structure:

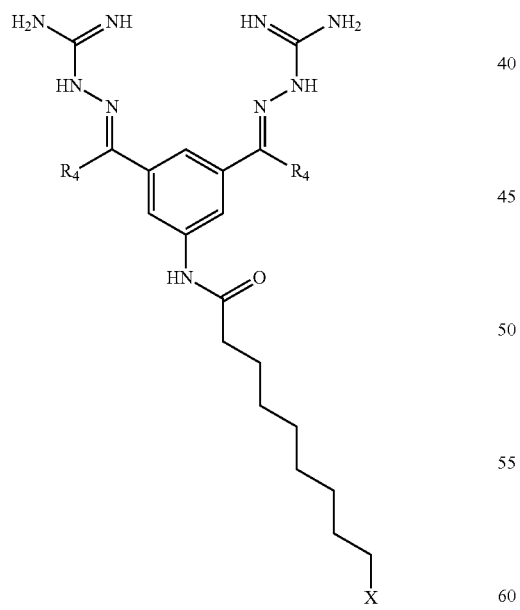

wherein each $R_4$ is, independently, chosen from —H or —CH$_3$, and wherein X=C2-C8 alkynyl, —CN$_3$, or —C(O)NHR wherein R is a di-substituted aryl, or is a pharmaceutically acceptable salt thereof.

In an embodiment, the guanylhydrazone compound comprises a compound having the structure:

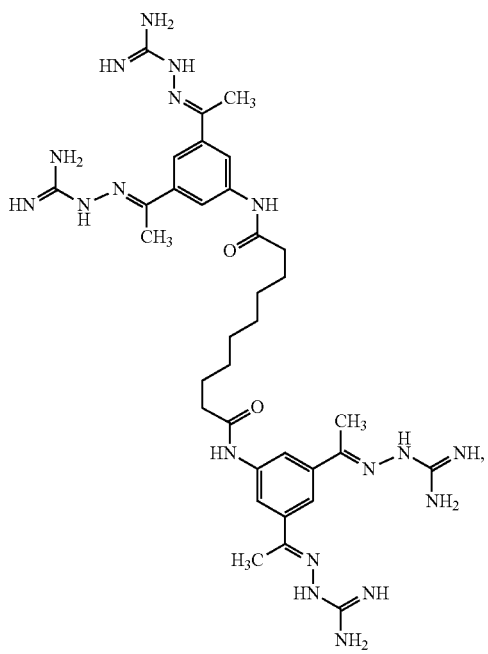

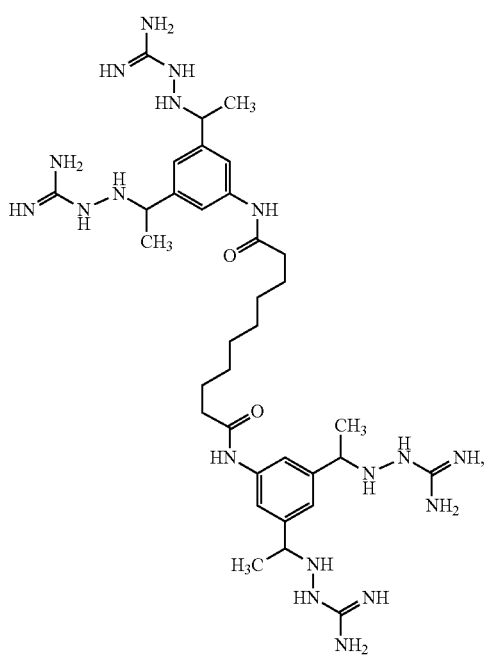

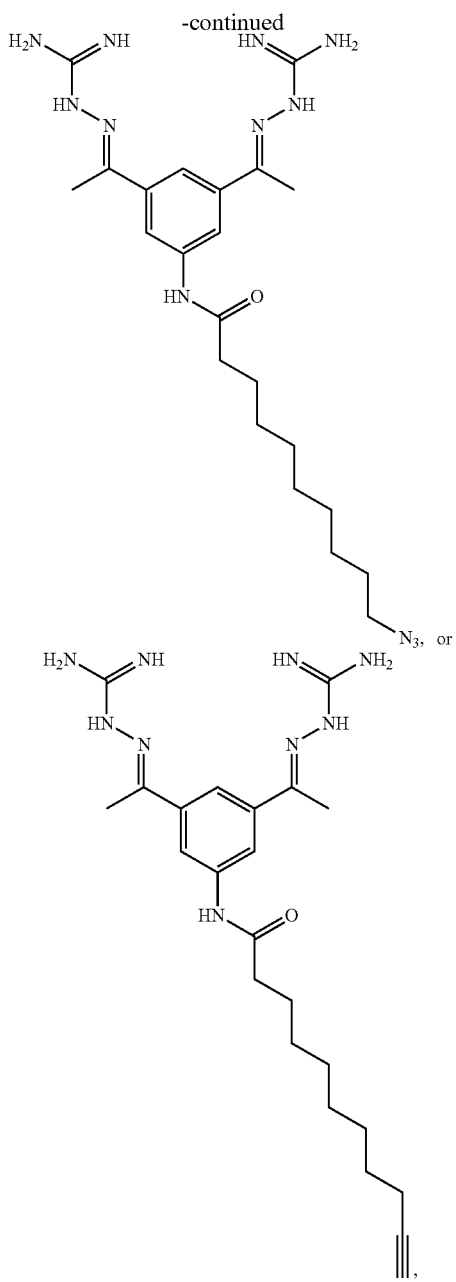

-continued

N₃, or or is a pharmaceutically acceptable salt thereof.

In an embodiment of the methods disclosed herein, the agent, subject, co-administration, delivery method or site and/or subject has one or more characteristics of the agents, subjects, co-administration, delivery methods or sites and/or subjects as described herein, including hereinabove.

Anti-tumor therapies are well known in the art and include radiotherapies, chemotherapies and anti-angiogenic therapies.

In a preferred embodiment of the methods and agents disclosed herein, the agent that inhibits microglia function is an organic molecule, comprising carbon to carbon bonds, of 2,000 daltons or less. In a preferred embodiment of the methods and agents disclosed herein, the agent that inhibits microglia function is an organic molecule, comprising carbon to carbon bonds, of between 500 and 1,000 daltons. In an embodiment of the methods and agents disclosed herein, the agent that inhibits microglia function is a macrophage inhibitor. In an embodiment of the methods and agents disclosed herein, the agent that inhibits microglia function inhibits cytokine production in a macrophage. In an embodiment of the methods and agents disclosed herein, the agent that inhibits microglia function inhibits microglia activation.

As used herein, "treating" an astrocytoma in a subject means ameliorating or reducing one or more characteristics or symptoms of the astrocytoma, including reducing tumor size, reducing tumor spread, and prolonging survival.

As used herein, "enhancing the efficacy" of brain tumor radiation therapy on an astrocytoma in a subject means enhancing one or more effects from the brain tumor radiation therapy as compared to, for example a control, for example an otherwise identical brain tumor radiation therapy without administration of the agent. Accordingly, achieving the same extent of effect on a measurable parameter, but at a lower dose of brain tumor radiation therapy, is considered enhancing the efficacy. Achieving a greater effect on a measurable parameter than at the same dose of brain tumor radiation therapy without the agent being administered is also considered enhancing the efficacy.

The phrase "and/or" as used herein, with option A and/or option B for example, encompasses the individual and separable embodiments of (i) option A, (ii) option B, and (iii) option A plus option B.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Introduction

There is mounting evidence that microglia (specialized brain-resident macrophages) play a significant role in the development and progression of glioblastoma tumors. Herein, guanylhydrazones (such as semapimod, a drug that selectively interferes with the function of macrophages and microglia) are investigated as a treatment for astrocytomas.

It is disclosed that in addition to stimulating glioblastoma cell invasion, microglia also promote glioblastoma cell proliferation and resistance to ionizing radiation (IR) in vitro. It was found that semapimod potently inhibits microglia-stimulated GL261 invasion, without affecting serum-stimulated glioblastoma cell invasion. Semapimod also inhibits microglia-stimulated resistance of glioblastoma cells to IR, but has no significant effect on microglia-stimulated glioblastoma cell proliferation. It was also found that intracranially administered semapimod strongly stimulates animal survival in combination with IR, but has no significant benefit in the absence of IR.

Semapimod (initially termed CNI-1493) is a multivalent guanylhydrazone small molecule that was developed as a targeted inhibitor of cytokine-inducible L-arginine transport in macrophages (11, 12). Remarkably, no significant effect of semapimod on cells from other lineages has been noted (13). Semapimod has been shown to have significant efficacy in several animal models of inflammation, including lethal sepsis (14). Importantly, semapimod has already been tested in a phase II clinical trial for Crohn's disease and was shown to be very well tolerated in humans (15). In this study, it was examined whether multivalent guanylhydrazones such as semapimod can blunt the stimulatory effect of microglia on the malignant behavior of glioblastoma cells, both in vitro and in a syngeneic orthotopic mouse model of malignant glioblastoma. It was found that semapimod sensitizes glioblastoma tumors to ionizing radiation by targeting microglia.

Materials and Methods

Model: An in vitro microglia-glioblastoma cell co-culture system consisting of microglia from C57Bl/6 mice and syngeneic GL261 glioblastoma cells was employed and orthotopic implantation of GL261 cells used as an in vivo model.

Cell Culture: Murine GL261 glioblastoma cells were obtained from the National Cancer Institute (Frederick, Md., USA) and normal murine microglia, isolated from C57Bl/6 mice (16), were obtained from S. Coniglio (Albert Einstein College of Medicine of Yeshiva University) (17). Both cultures were maintained in Macrophage Serum-Free Medium (MSFM; Life Technologies Corporation) with 10% fetal calf serum. Microglia were supplemented with 10 ng/mL recombinant mouse granulocyte macrophage-colony-stimulating factor (GM-CSF) (R&D Systems). All cultures were grown at 37° C. in a humidified atmosphere of 5% $CO_2$, 95% air. Cell lines were tested for the presence of contaminating mycoplasma during experimentation.

Reagents: Semapimod was produced in-house by Dr. Yousef Al-Abed and prepared as a stock concentration of 20 mM in 7% DMSO and $ddH_2O$. It was diluted for experiments using Dulbecco's phosphate-buffered saline (PBS) to concentrations required.

Invasion Assays: Glioblastoma and microglial cells were labelled with cell tracker green CMFDA and with cell tracker red CMTPX, respectively, and then embedded in 50 µL of 10 mg/mL basement membrane extract (BME) (Trevigen). The mixture was then placed in a transwell insert (previously coated with 1 µg/mL fibronectin on the bottom side of the 8 µm filter to maintain adhesion of the cells that invaded through the filter) and allowed to polymerize for 30 min at 37° C. Subsequently, serum free medium was added to both wells. To maintain constant cell numbers, cells were plated at a density per invasion chamber of $15 \times 10^4$ GL261 cells and $5 \times 10^4$ microglia cells in MSFM. Semapimod or its diluent was added at varying concentrations into the BME and in the media above and below the transwell. Invasion chambers were incubated for 48 h and subsequently fixed in 3.7% formaldehyde in phosphate-buffered saline (PBS). The gel in the transwell inserts was carefully removed. Invaded glioblastoma cells were imaged with a Zeiss Axiovision inverted microscope and a 10× objective. All invaded cells were counted.

To measure the invasion of microglia toward glioblastoma cells in vitro, a variant of the glioblastoma cell invasion assay was used. First, $15 \times 10^4$ G1261 cells were plated in MSFM medium overnight and subsequently were placed in serum free medium. Subsequently, $5 \times 10^4$ microglia cells were embedded in 50 µL, of 10 mg/mL BME with or without 200 nM semapimod, placed in a 8 µm transwell (previously coated with 1 µg/mL fibronectin on the bottom side of the 8 µm filter to maintain adhesion of the cells that invaded through the filter) and allowed to polymerize for 30 min at 37° C. The transwell chambers were then placed above the previously plated GL261. After 48 h of incubation, the chambers were fixed in 3.7% formaldehyde in PBS.

The cells were stained with 0.2% crystal violet in 2% ethanol. The remaining BME was carefully removed and the inserts were allowed to dry. Cells attached to the bottom of the filter were imaged as for the invasion assay and the total number of invaded microglia was determined.

Colony Formation Assay: G1261 cells and microglia were labeled as described for the invasion assay and were co-cultured in serum overnight and then changed to serum free medium for 48 h in the absence of serum at a 1:1 ratio at a density of $5 \times 10^5$ per well of a 6-well plate in the presence or absence of 200 nM semapimod. Subsequently, cells were subjected to 3 Gy of X-ray irradiation using a Radionics 160 kV irradiator. Two days after irradiation, cells were trypsinized, counted using a fluorescence microscope and 500 GL261 cells were plated in 6 cm dishes containing 10% FBS MSFM medium. Colony formation was allowed to proceed for 12 days, with medium changes every other day. Subsequently, the cells were fixed in 3.7% formaldehyde in PBS and stained with 0.2% (w/v) sulpharhodamine B (SRB) dye in 1% acetic acid for 20 min. The dishes were washed with 1% glacial acetic acid and allowed to dry. Plates were scanned and processed using Photoshop 5 (Adobe). Images were changed to grayscale and background threshold intensity was set. Colonies were counted automatically by Image J (rsbweb.nih.gov/ij/) and the numbers graphed.

Proliferation Assay: 50,000 GL261 cells were cultured overnight in the absence or presence or microglia (50,000 or 150,000) in serum-containing medium and subsequently cultured in the presence or absence of 200 nM semapimod in a 6-well dish in serum-free conditions. Microglia were added in a ratio of 1:1 or 1:3 GL261:microglia. After 72 h of incubation, plates were washed in PBS and fixed in 3.7% formaldehyde in PBS. In initial experiments, the microglia were stained with tomato lectin for 45 mins and stained all nuclei with DAPI. Ten fluorescence micrographs of each culture were taken with a Zeiss Axiovert-based imaging system. Counting of the cells showed that the number of the microglia did not change over the observation period of 3 days. Therefore in subsequent experiments the cells were stained with SRB as described for the colony formation assay. After drying, the plates were de-stained with 500 µL of 10 mM Tris base (Sigma). Eluted SRB was measured by absorbance at 490 nm.

Animal Experiments: All procedures involving mice were conducted in accordance with the National Institutes of Health regulations concerning the use and care of experimental animals. The study of mice was approved by the Institutional Animal Care and Use Committee (IACUC) of the Feinstein Institute. First, 8 week old male C57BL/6J mice were inoculated in the right caudate putamen with GL261 cells. Briefly, animals were placed in a stereotactic frame after pre-anesthesia exposure in a box of 5% isoflurane. Deep anesthesia was maintained on the frame at approximately 2% isoflurane and 2% $O_2$. A burr hole was drilled 1 mm anterior and 2.5 mm to the right of the bregma. With the aid of the stereotactic frame, GL261 cells ($2 \times 10^4$ cells suspended in 1 µL) were injected with a Hamilton syringe at a depth of 3 mm over a one min time period. Subsequently, the syringe was left in place for 1 min to prevent reflux.

Seven days after implantation of the GL261 cells, an osmotic pump (Alzet, Durect) filled with either 0.42 mg/ml solution of semapimod or vehicle was implanted in a subcutaneous pocket on the dorsal flank of the animal. A catheter with attached cannula delivered the drug intracranially over a period of 2 weeks, at a steady rate of 0.25 µl/h, which is equivalent to a dose of 6 mg/kg/day, assuming no blood-brain barrier permeability of the drug. Starting one day after pump implantation, animals were given 2 Gy whole brain irradiation every other day over a period of 10 days (10 Gy total). Animals that lost greater than 20% in body weight or displayed paralysis and/or lack of grooming, were deemed moribund and euthanized immediately.

Brains from mice-bearing tumors were frozen on dry ice and stored at −80° C. until processing. The brain was sliced using a cryostat at −20° C. at a thickness of 40 μm (for tumor sizing) or 8 μm for immunohistochemistry. Slices were placed on pre-coated poly-1-lysine slides (Superfrost, Fisher) and fixed in 3.7% formaldehyde in PBS. Sections were stained with Harris-modified haematoxilin solution. Activated microglia were visualized with an Iba1 antibody (Wako). Tumor cell invasion was determined by counting the number of Ki67 (Millipore) positive nuclei located beyond the tumor border. The border was outlined by determining where the bulk of the tumor material was found by Ki67 staining Tumor size was determined as the area of the largest cross section of the tumor, multiplied by the depth of the tumor.

The cell density of the tumor was calculated by counting the total number of cells in 10 fields taken over different sections and multiplying the tumor area by the thickness of the slice (8 μm) to obtain total number of cells in a tumor section. This was then divided by the volume of the tumor section to obtain the number of cells per unit volume. To obtain the total number of cells in a tumor, the cell density was multiplied by the calculated volume of the tumor.

Results

Semapimod inhibits microglia-stimulated glioblastoma cell invasion: In order to examine the effect of microglia on the malignant properties of glioblastoma cells, GL261 murine glioblastoma cells were used along with syngeneic microglia isolated from C57Bl/6 mice, a model system that has been extensively used to study the reciprocal interaction between glioblastoma cells and microglia (9, 10, 17).

A defining feature of malignant glioblastoma is the diffuse invasion of tumor cells into the surrounding parenchyma and microglia have been shown to strongly promote this activity (9, 17-20). To determine the effect of microglia on the invasive properties of glioblastoma cells, a novel 3-dimensional microglia-glioblastoma co-culture assay was designed that provides a better approximation of the in vivo setting than a 2-dimensional configuration. Fluorescently labeled cells were embedded in reconstituted extracellular matrix (BME) in the absence of added serum at a ratio of 3:1 glioblastoma cells to microglia and subsequently placed in transwells provided with an 8 μm pore filter. Using this assay, it was observed that microglia stimulate GL261 invasion up to 5 fold and that semapimod interferes with this effect with an $IC_{50}$ of less than 50 nM (FIG. 1A), similar to the $IC_{50}$ of semapimod in inflammatory cytokine release from macrophages (11).

Importantly, semapimod, even at a concentration of 10 μM, does not affect serum-stimulated GL261 invasion, underlining the selectivity of semapimod for cells from the monocytic lineage (FIG. 1B).

Semapimod inhibits glioblastoma-induced microglia invasion in vitro: Microglia extensively infiltrate glial tumors (5-7). To examine whether semapimod can also inhibit migration of microglia towards glioblastoma cells, an in vitro transwell invasion assay was established by measuring the number of microglia that invade through a 3-dimensional extracellular matrix toward glioblastoma cells. The presence of GL261 cells in the bottom well was observed to strongly stimulate microglia invasion, by approximately 12 fold (FIG. 1C). This stimulatory effect is abolished by semapimod, with an $IC_{50}$ of approximately 60 nM.

Figures 2A, 2B:
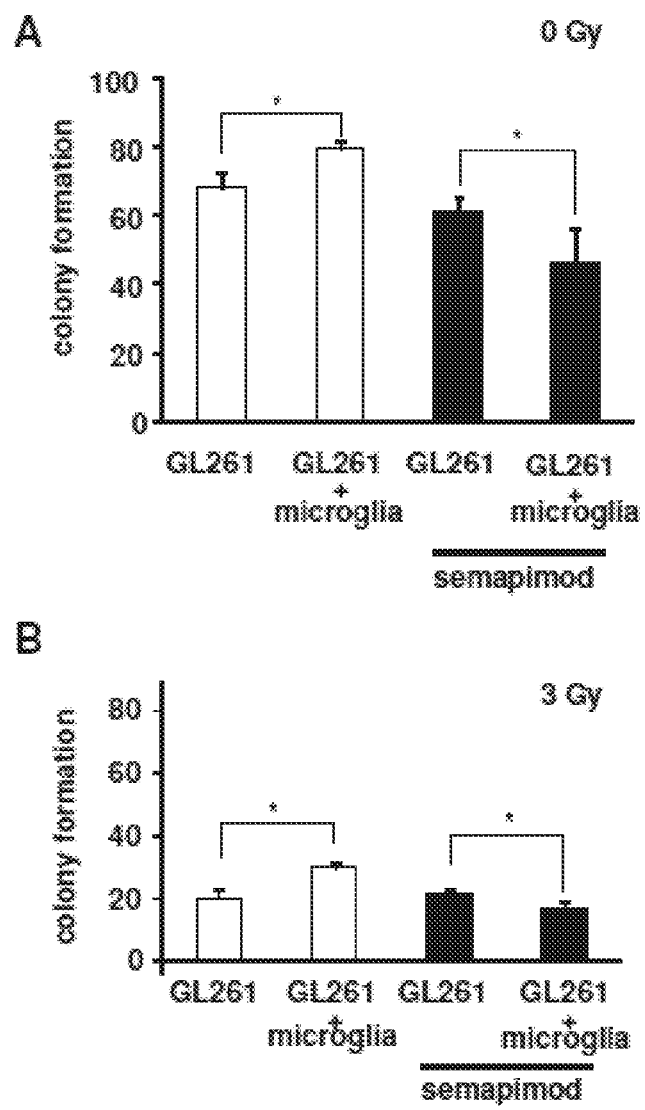
FIG. 2A-2B. Semapimod removes microglial-induced radioprotection on GL261 in vitro. GL261 cells were cultured in the presence or absence of microglia and in the presence or absence of 200 nM of semapimod, followed by a colony formation assay. (A) Colony formation assay of GL261 after treatment with microglia and semapimod. (B) Determination of survival of GL261 after treatment with 3Gy irradiation, microglia and semapimod. Data shown represent the average+/−SEM of 3 independent experiments. *: p<0.05 student's 2 tailed t-test.

Semapimod inhibits microglia-stimulated glioblastoma cell survival: A critical problem of malignant glioblastoma is its strong resistance to ionizing radiation (IR) and other therapeutic modalities (21). The role of microglia in glioblastoma cell survival has not been studied thus far. It was therefore examined whether microglia can enhance the survival of GL216 cells after IR and whether semapimod interferes with this function. GL261 cells were plated either in the presence or absence of microglia with or without semapimod (200 nM) for 2 days, followed by radiation treatment (3 Gy). Two days later, glioblastoma cell viability was assayed using a standard colony formation assay. It was observed that co-culturing GL261 cells with microglia in the absence of radiation slightly, but significantly, stimulates their survival and that semapimod abolishes this (FIG. 2A). In the presence of radiation, the stimulatory effect of microglia on glioblastoma cell survival is more marked (50%) and this effect is also abolished by semapimod (FIG. 2B). In line with the selectivity of semapimod for cells from the monocytic lineage, semapimod does not affect the survival potential of glioblastoma cell monocultures. Thus, taken together, these data indicate that semapimod inhibits microglia-stimulated glioblastoma cell survival by modulating the activation state of the microglia.

Figure 3:
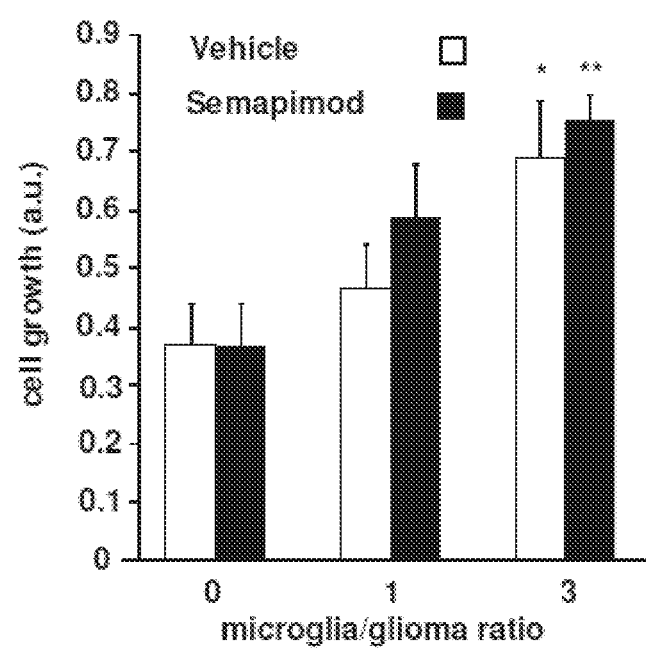
FIG. 3. Semapimod does not affect microglia-stimulated growth of glioblastoma cells in vitro. GL261 cells were cultured in the presence or absence of microglia at the indicated ratios, in the presence and absence of 200 nM semapimod. Cell growth over a period of 3 days was determined using the SRB method. Data shown represent the average+/−SEM of 3 independent experiments. *: p<0.05, **: p<0.01 Student's 2 tailed t-test.

Semapimod does not affect microglia-stimulated glioblastoma cell proliferation: Microglia have been shown to slightly stimulate glioblastoma cell proliferation and therefore it was also desired to examine whether semapimod inhibits this effect. FIG. 3 shows that microglia stimulate GL261 cell proliferation in a fashion that depends on the microglia-glioblastoma cell ratio. However, semapimod (200 nM) does not affect the microglia-stimulated glioblastoma cell proliferation.

Figures 4A, 4B, 4C, 4D:
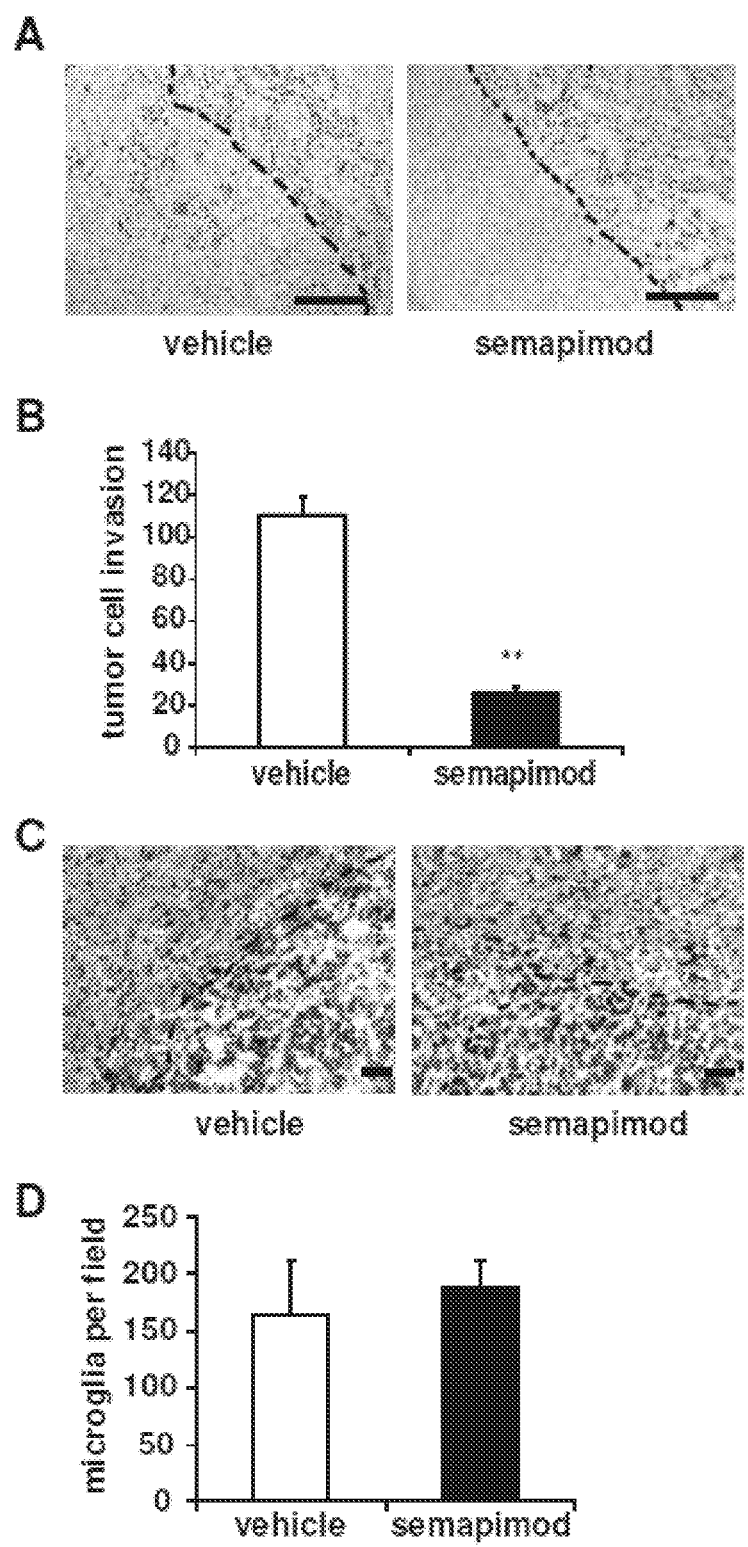
FIG. 4A-4D. Semapimod inhibits glioblastoma cell invasion in vivo. GL261 cells were orthotopically implanted into C57Bl/6 mice. Starting 7 days after cell inoculation, the mice were treated intracranially for 1 week with semapimod, delivered via an osmotic pump. (A) Micrographs of tumor sections illustrating inhibition of GL261 cell invasion by semapimod. GL261 cells were visualized using Ki67 staining. The tumor borders are outlined. Scale bar represents 200 μm. (B) Quantification of GL261 cell invasion normalized to the length of the tumor border. Data shown represent the average+/−SEM of 5 different tumors. **: p<0.01 Student's 2 tailed t-test. (C) Micrographs illustrating infiltration of microglia into GL261 tumors. Activated microglia were visualized using Iba1 staining (D) Quantification of Iba1+ microglia infiltrated into the tumor. Scale bar represents 100 μm. Data shown represent the average+/−SEM of 5 different tumors.

Semapimod strongly inhibits tumor cell invasion in vivo: To evaluate the effect of semapimod on the malignant behavior of glioblastoma in vivo, orthotopic implantation of GL261 cells into syngeneic C57Bl/6 mice was used. This model displays all the pathological hallmarks of glioblastoma and is often used for examining the role of microglia in glioblastomagenesis and for pre-clinical evaluation of immunomodulatory therapies (9, 10, 17, 22). In order to identify an effective dose of semapimod, studies were performed and the minimal concentration that maximally inhibited tumor invasiveness one week after start of treatment was chosen. Animals were inoculated with $2 \times 10^4$ GL261 cells into the right caudate putamen. To deliver semapimod, an osmotic pump was used that was implanted subcutaneously in the dorsal flank of the animal and fed a transcranial cannula that was inserted into the tumor. In order to mimic a therapeutic setting, tumors were allowed to develop for 1 week before the onset of treatment. To score tumor cell invasion, brain sections were probed for the presence of proliferative antigen Ki67. In line with the in vitro observations, semapimod, at a dose that is equivalent to 6 mg/kg/day, strongly inhibited tumor invasion. Whereas control tumors display diffuse edges and extensive tumor cell invasion into the surrounding parenchyma, semapimod-treated tumors have a sharply demarcated border (FIG. 4A). Quantification of the invading tumor cells revealed that semapimod inhibits tumor cell invasion by more than 75% (FIG. 4B).

As the in vitro observations showed that semapimod strongly inhibits invasion of microglia toward GL261 cells, it was also examined whether tumor sections for the infiltration of microglia using Iba1 staining (FIG. 4C). No significant difference in the number of microglia per tumor area could be detected, however (FIG. 4D). The most likely interpretation for this finding is that semapimod treatment was started 7 days after the implantation of the tumor cells, a time at which microglia infiltration already has occurred (23).

Figures 5A, 5B, 5C:
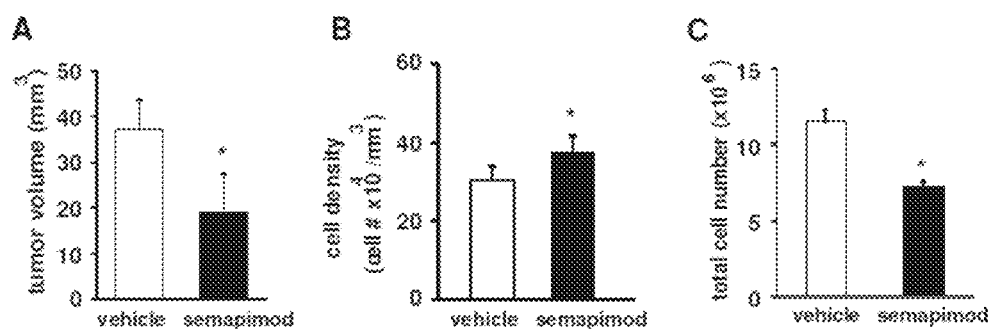
FIG. 5A-5C. Semapimod inhibits tumor growth in vivo. GL261 cells were implanted and mice were treated as described in FIG. 4. (A) Quantification of tumor volume. Data shown represent the average+/−SEM of 5 different tumors. (B) Quantification of tumor cell density. Data shown represent the average+/−SEM of 5 different tumors. (C) Quantification of total tumor cell number. Data shown represent the average+/−SEM of 5 different tumors. *: p<0.05 student's 2 tailed t-test.

As semapimod does not affect GL261 cell proliferation in vitro, it was surprising to find that semapimod treatment causes a robust inhibition of tumor size, two weeks after tumor cell inoculation (FIG. 5A). Interestingly, the treated tumors also display a small but significant increase in tumor cell density (FIG. 5B), possibly caused by the strong inhibitory effect of semapimod on tumor cell invasion. Still, the estimated total number of cells in semapimod treated tumors is significantly less than that in control tumors, indicating that semapimod indeed diminishes the proliferation potential of the tumor cells in vivo (FIG. 5C). The discrepancy between the in vitro and the in vivo tumor cell proliferation data may be due to the fact that the in vivo observations reflect the cumulative effect of many cell divisions, thereby possibly amplifying small differences in cell proliferation, that are not detectable in the in vitro experiments.

Figure 6:
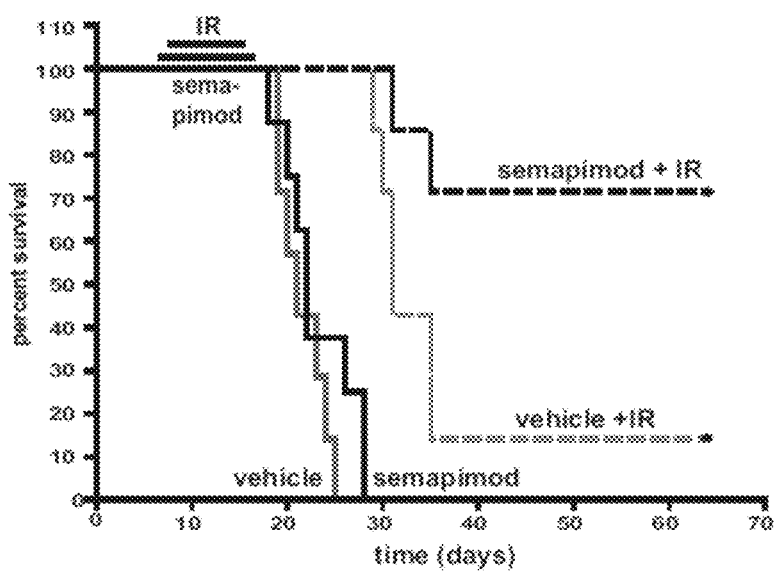
FIG. 6. Semapimod increases survival of glioblastoma-bearing mice in conjunction with ionizing radiation. C57Bl/6 mice were injected orthotopically with GL261 cells. Starting 7 days after cell inoculation, the mice were treated intracranially for 2 weeks with semapimod, delivered via an osmotic pump. Starting on day 8, animals were given 2 Gy whole brain irradiation every other day over a period of 10 days (10 Gy total). *: p<0.05. Chi square test, with 3 degrees of freedom.

Semapimod strongly enhances the therapeutic efficacy of ionizing radiation in a syngeneic orthotopic mouse model of glioblastoma: To determine the effect of semapimod on the survival of glioblastoma-bearing mice and to examine the effect of semapimod on radiation resistance in vivo, 4 groups of animals were randomized to receive semapimod or diluent in the absence or presence of 10 Gy fractionated whole brain irradiation. It was observed that in the absence of radiation, semapimod does not significantly prolong survival (median survival of 22 days for semapimod-treated animals versus 20 days for controls) (FIG. 6). However, whereas radiation alone increased median survival by 12 days, most of the irradiated animals that were treated with semapimod survived at least 40 days beyond the median survival time of control animals and had no detectable tumors as judged by histological analysis (data not shown). These observations indicate that semapimod strongly sensitizes GL261 tumors to radiation.

Discussion

Here it is shown that the immunomodulatory drug semapimod strongly inhibits microglia-stimulated glioblastoma cell invasion and survival in vitro. It is also shown that semapimod markedly enhances the survival of glioblastoma-bearing mice in conjunction with radiation therapy, but not as monotherapy, where it has only a marginal benefit. The observations that semapimod does not affect the invasiveness and survival potential of glioblastoma cells in monoculture, strongly suggest that the inhibitory effects of semapimod on microglia-stimulated glioblastoma cell invasion and survival are due to targeting the microglia compartment. This is in line with previous data showing that semapimod is selective for cells derived from the monocytic lineage, i.e. microglia, macrophages and dendritic cells, but not T cells (13, 24). The mechanism of action of semapimod remains to be elucidated.

It is noted that semapimod has been extensively used as an anti-inflammatory agent (11, 12, 25, 26). Thus, the results that semapimod sensitizes tumors to radiation therapy, may seem paradoxical, as the immune system, in general, is thought to counteract tumor formation. Hitherto, however, the role of microglia in the malignant behavior of glioblastoma cells has largely focused on the invasiveness of the tumor cells (4, 5) and the effect of microglia on the survival properties of glioblastoma cells has not been investigated.

Here it is reported that microglia exert a small, but significant, stimulatory effect on the survival of glioblastoma cells that are challenged by ionizing radiation and that semapimod inhibits this effect. In line with this result, it is found that semapimod treatment markedly extends the survival of glioblastoma bearing animals that are treated with ionizing radiation. The relatively large effect size of semapimod treatment observed in vivo may be explained by the use of a fractionated radiation regimen (5 doses of 2 Gy, every other day), which is expected to magnify the survival benefit seen in the single dose of irradiation in the in vitro setting.

Radiosensitization has been observed by depleting macrophages in a subcutaneous melanoma model (28) and a marked enhancement of the inhibitory effect of paclitaxel on mammary tumor pulmonary metastasis has been observed with a CSF1R inhibitor that blocks macrophage recruitment to the tumor (29). Notably, in all these cases, targeting the tumor-associated microglia/macrophage compartment on its own showed little or no therapeutic benefit. These observations strongly suggest that the microglia/macrophage compartment plays a critical role in therapeutic resistance and that targeting this compartment in combination with other therapeutic modalities is likely to be of significant clinical benefit.

Additionally, it was found that semapimod has a marked inhibitory effect on glioblastoma tumor cell invasion both in vitro and in vivo. These observations are in line with previous reports that have demonstrated that interference with the function of microglia or depletion of the microglial compartment has a strong inhibitory effect on glioblastoma cell invasion (9, 17). Interestingly however, the marked inhibition in tumor invasiveness caused by semapimod is not accompanied by a significant increase in survival of glioblastoma-bearing mice. Combined treatment with an antibody or antibody fragment that inhibits vascular endothelial growth factor A (such as bevacizumab), which has been shown to enhance the invasive behavior of glioblastoma tumors (31, 32), is likely advantageous.

An attractive feature of semapimod is that it is shown to be very well tolerated in humans and displays a good safety profile. Thus, the data indicate the utility of repositioning microglial inhibitors, such as guanylhydrazones like semapimod, as an immunomodulator for the treatment of glioblastoma, as up-front adjuvant to standard therapy, and/or concurrent with other anti-tumor therapies, for example radiation and/or chemotherapies, such as DNA alkylating/methylating chemotherapeutics (e.g., temozolomide) (1).

Example 2

Introduction

Tumor-associated macrophages (TAMs) are immune cells that have recently been implicated in promoting tumor growth and invasion. TAMs may play a role in the malignant progression of the childhood soft tissue cancer known as Ewing's Sarcoma through the promotion of angiogenesis, tissue remodeling, immune suppression and cellular proliferation. Current treatment strategies for Ewing's Sarcoma, including surgery, radiation and chemotherapy, target tumor cells to limit disease progression. However, genetic heterogeneity throughout a tumor may lead to therapeutic resistance, causing advanced disease.

Herein is disclosed a method of inhibiting genetically stable stromal elements within the tumor microenvironment using guanylhydrazones (such as agent CNI-1493) to decrease recurrent and metastatic Ewing's Sarcoma, thus improving the prognosis of patients diagnosed with this disease. Guanylhydrazones (such as agent CNI-1493) may work by de-activating TAMs, thereby decreasing the malignant development of Ewing's Sarcoma to improve patient prognosis.

Materials and Methods

In vivo, human ES cells (SK-NEP1) were surgically implanted into the left kidney of athymic mice. Mice were treated for 7 weeks with CNI-1493 or vehicle. Lung parenchyma was assessed for metastases utilizing both H&E and immunohistochemistry for the ES-specific CD99 and endothelial-specific CD31 markers. In vitro, primary macrophages isolated from human blood were polarized to M1 or M2 phenotypes by exposure to GM-CSF or M-CSF and activated with IFN-γ and LPS or IL-4. Cells were co-cultured with polarized macrophages and underwent proliferation and invasion assays in the presence or absence of CNI-1493.

Results: In vivo, overall metastatic tumor burden was significantly decreased in CNI-1493-treated mice (p<0.05). Primary tumor size was not affected in CNI-1493-treated mice versus control (5.7±3.3 g vs. 7.0±5.2 g, p=0.54). Immunohistochemistry of lung tissue revealed micrometastases confined to the vasculature with CNI-1493 treatment, compared to larger metastases with extensive parenchymal invasion in controls. In vitro, ES cellular invasion was significantly enhanced in the presence of M2 (p<0.01), but not M1 macrophages and this effect was strongly decreased by CNI-1493 treatment (p<0.01). ES cellular proliferation was inhibited in the presence of M1 (p<0.01), but not M2 macrophages and was unaffected by CNI-1493 treatment.

Discussion

Figure 7:
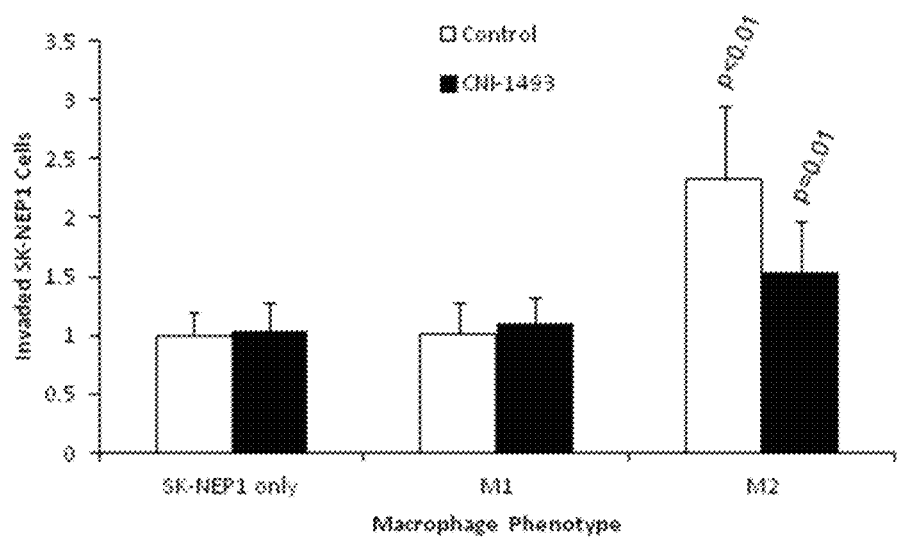
FIG. 7. CNI-1493 inhibits tumor invasion in vitro through in the presence of macrophages. When co-cultured with SK-NEP1, macrophages polarized to express the M2 phenotype induced increased tumor cell invasion. This increase in invasion was reversed when co-cultures were exposed to 200 nM CNI-1493. Error bars represent standard deviation.

When the Ewing's Sarcoma cell line SK-NEP1 was grown in co-culture with human primary macrophages of various phenotypes, treatment with CNI-1493 was found to significantly reduce tumor cell invasion through a basement membrane. This suggests that the signaling of tumor-associated macrophages, which normally induce tumor cell invasion and malignant progression, is inhibited by treatment with CNI-1493 (FIG. 7). These in vitro findings of decreased invasion have been recapitulated in vivo in an animal model of metastatic Ewing's Sarcoma. Intraperitoneal administration of CNI-1493 at a dose of 5 mg/kg/day was found to both significantly reduce primary tumor size as well as overall metastatic disease burden (FIGS. 8a and 8b). This is in contrast to the breast cancer findings of Erin et al. (Regulatory Peptides 179:101-108 (2012)), where a strong distant anti-metastatic effect was noted in breast cancer in contrast to its effect on primary tumor growth. Furthermore, there was a trend towards decreased incidence of metastatic disease in CNI-1493-treated mice (52% vs 21%, p=0.055). Although the mechanism is as of yet still unclear, histologic examination reveals that metastases in CNI-1493-treated mice were limited to the intravascular space, perhaps indicating that CNI-1493 impedes tumor cell extravasation into the parenchyma of the metastatic niche (FIG. 9).

Treatment of Ewing's Sarcoma currently utilizes a multimodal approach, including chemotherapy, radiation and surgery to eradicate the primary tumor and limit disease progression. Virtually all patients who die of Ewing's sarcoma succumb to metastatic disease despite excellent control of the primary tumor site, a finding ubiquitous to virtually all pediatric solid tumors. In addition, current therapy is toxic and disabling, and in patients with metastatic disease, often ineffective in preventing death. The addition, up front, of guanylhydrazones such as CNI-1493 to the standard therapeutic regimen may help prevent Ewing's Sarcoma metastatic progression without toxic or disabling side effects. Prevention of future distant metastases is the most effective way to improve survival and continuous therapy with CNI-1493, even after chemo-radiation and surgery have achieved primary tumor control, may be critical.

In summary, macrophages expressing the pro-tumor M2 phenotype induce ES cellular invasion. Treatment with the macrophage inhibitor CNI-1493 decreases ES invasion in vitro and in vivo, resulting in less invasive tumors with reduced metastatic potential.

Example 3

Figure 10:
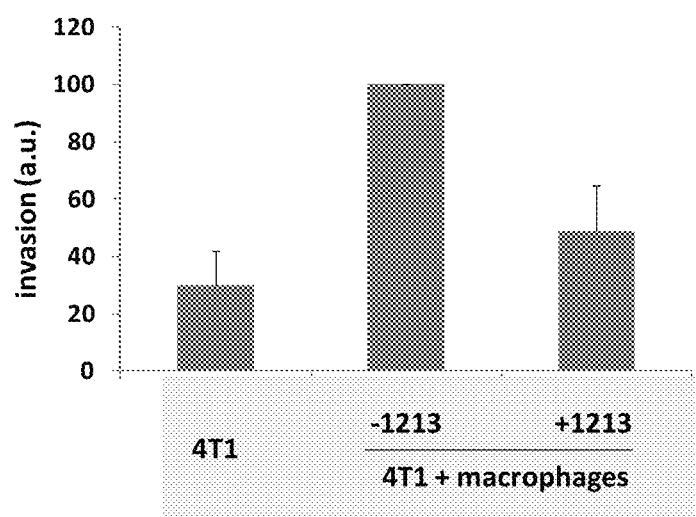
FIG. 10. CP1213 (a reduced-form derivative of CNI-1493) inhibits macrophage-stimulated invasion of 4T1 breast cancer cells. 4T1 cells ($4\times10^5$) and RAW 264.7 macrophages ($1.33\times10^5$) were embedded in 50 μl of basement membrane extract in the presence or absence of CP1213 (1 μM), layered in a 24-well transwell and incubated for 28 h. The number of invading 4T1 cells was determined. Data shown represent the average+/−SD of 4 independent experiments, each performed in duplicate. *p<0.01.

The guanylhydrazone CP1213 (a reduced form of CNI-1493) inhibits macrophage-stimulated invasion of 4T1 breast cancer cells. 4T1 cells ($4 \times 10^5$) and RAW 264.7 macrophages ($1.33 \times 10^5$) were embedded in 50 µl of basement membrane extract in the presence or absence of CP1213 (1 µM), layered in a 24-well transwell and incubated for 28 h. The number of invading 4T1 cells was determined. Data are shown in FIG. 10 and represent the average+/−SD of 2 independent experiments, each performed in duplicate. The data support a method of treating a tumor, by inhibiting cell invasion processes with guanylhydrazones.

Example 4

Figure 11:
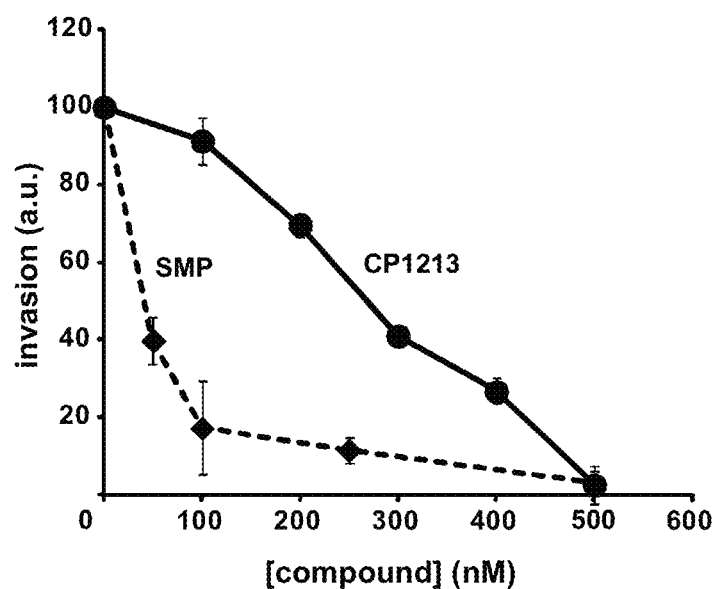
FIG. 11. Concentration dependence of the inhibitory effects of semapimod (CNI-1493) and CP1213 on microglia-stimulated invasion of glioma cells. GL261 cells ($3\times10^5$) and microglia ($1.5\times10^5$) were embedded in 50 μl of basement membrane extract in the presence of the indicated concentrations of semapimod (SMP) and CP1213, layered in a 24-well transwell and incubated for 48 h. The number of invading GL261 cells was determined. Data shown represent the average+/−SD of between 2 and 5 independent experiments, each performed in duplicate.

The concentration dependence of the inhibitory effect of semapimod or CP1213 was investigated on microglia-stimulated invasion of glioma cells. GL261 cells ($3 \times 10^5$) and microglia ($1.5 \times 10^5$) were embedded in 50 µl of basement membrane extract in the presence of the indicated concentrations of semapimod (SMP) and CP1213, layered in a 24-well transwell and incubated for 48 h. The number of invading GL261 cells was determined. Data are shown in FIG. 11 and represent the average+/−SD of between 2 and 5 independent experiments, each performed in duplicate. The data support a method of treating a glioma, by inhibiting microglia-stimulated invasion processes with guanylhydrazones.

Figure 12:
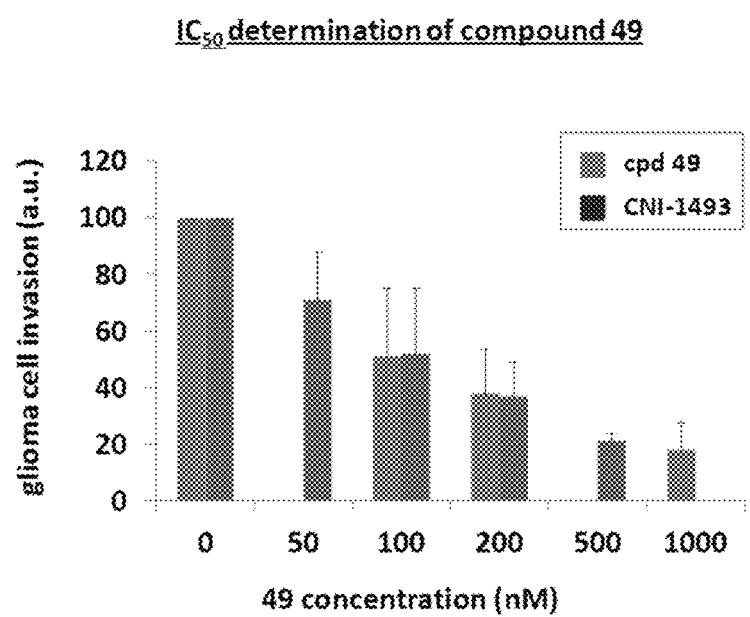
FIG. 12. Functional IC$_{50}$ determination for compound 49 (a divalent form derivative of CNI-1493).

In addition, the $IC_{50}$ of another guanylhydrazone (compound 49, which is the divalent form of the tetravalent CNI-1493) for inhibition of glioma cell invasion was compared with that of CNI-1493. $9 \times 10^4$ glioblastoma (U87R) and $3 \times 10^4$ microglial (CHME5) cells were embedded in 50 µL of 10 mg/mL basement membrane extract (BME) (Trevigen). The mixture was then placed in a transwell insert (previously coated with 1 µg/mL fibronectin on the bottom side of the 8 µm filter to maintain adhesion of the cells that invaded through the filter) and allowed to polymerize for 30 min at 37° C. Subsequently, Macrophage Serum-Free Medium (MSFM; Life Technologies Corporation) was added to both wells. Compound 49, semapimod or diluent was added at varying concentrations into the BME and in the media above and below the transwell. Invasion chambers were incubated for 48 h and subsequently fixed in 3.7% formaldehyde in phosphate-buffered saline (PBS), followed by staining with crystal violet. The gel in the transwell inserts was carefully removed. Subsequently, invaded glioblastoma cells were imaged with a Zeiss Axiovision inverted microscope and a 10× objective. All invaded glioblastoma cells (readily distinguished from the microglia based on cell shape) were counted. Shown in FIG. 12 are the means+/−SD of 4 wells, comprising 2 independent experiments.

REFERENCES

1. Stupp R, Mason W P, van den Bent M J, et al. Radiotherapy plus concomitant and adjuvant temozolomide for glioblastoma. *N Engl J Med.* 2005; 352(10):987-996.
2. Ransohoff R M and Cardona A E. The myeloid cells of the central nervous system parenchyma. *Nature.* 2010; 468 (7321):253-262.
3. Hanisch U K and Kettenmann H. Microglia: active sensor and versatile effector cells in the normal and pathologic brain. *Nat Neurosci.* 2007; 10(11):1387-1394.
4. Li W and Graeber M B. The molecular profile of microglia under the influence of glioma. *Neuro Oncol.* 2012; 14(8):958-978.
5. Charles N A, Holland E C, Gilbertson R, Glass R, and Kettenmann H. The brain tumor microenvironment. *Glia.* 2011; 59(8):1169-1180.
6. Roggendorf W, Strupp S, and Paulus W. Distribution and characterization of microglia/macrophages in human brain tumors. *Acta Neuropathol.* 1996; 92(3):288-293.
7. Komohara Y, Ohnishi K, Kuratsu J, and Takeya M. Possible involvement of the M2 anti-inflammatory macrophage phenotype in growth of human gliomas. *J Pathol.* 2008; 216(1):15-24.
8. Kostianovsky A M, Maier L M, Anderson R C, Bruce J N, and Anderson D E. Astrocytic regulation of human monocytic/microglial activation. *J Immunol.* 2008; 181(8): 5425-5432.
9. Markovic D S, Vinnakota K, Chirasani S, et al. Gliomas induce and exploit microglial MT1-MMP expression for tumor expansion. *Proc Natl Acad Sci USA.* 2009; 106 (30):12530-12535.
10. Zhai H, Heppner F L, and Tsirka S E. Microglia/macrophages promote glioma progression. *Glia.* 2011; 59(3):472-485.
11. Bianchi M, Bloom O, Raabe T, et al. Suppression of proinflammatory cytokines in monocytes by a tetravalent guanylhydrazone. *J Exp Med.* 1996; 183(3):927-936
12. Bianchi M, Ulrich P, Bloom 0, et al. An inhibitor of macrophage arginine transport and nitric oxide production (CNI-1493) prevents acute inflammation and endotoxin lethality. *Mol. Med.* 1995; 1(3):254-266.
13. Bjork L, Tracey K J, Ulrich P, et al. Targeted suppression of cytokine production in monocytes but not in T lymphocytes by a tetravalent guanylhydrazone (CNI-1493). *J Infect Dis.* 1997; 176(5):1303-1312.
14. Lowenberg M. Proximal signaling molecules as potential targets for anti-inflammatory therapy. *Curr Opin Drug Discov Devel.* 2007; 10(5):560-564.
15. Dotan I, Rachmilewitz D, Schreiber S, et al. A randomised placebo-controlled multicentre trial of intravenous semapimod HCl for moderate to severe Crohn's disease. *Gut.* 2010; 59(6):760-766.
16. Dobrenis K. Microglia in cell culture and in transplantation therapy for central nervous system disease. *Methods.* 1998; 16(3):320-344.
17. Coniglio S J, Eugenin E, Dobrenis K, et al. Microglial stimulation of glioblastoma invasion involves epidermal growth factor receptor (EGFR) and colony stimulating factor 1 receptor (CSF-1R) signaling. *Mol Med.* 2012; 18(1):519-527.
18. Bettinger I, Thanos S, and Paulus W. Microglia promote glioma migration. *Acta Neuropathol.* 2002; 103(4):351-355.
19. Wesolowska A, Kwiatkowska A, Slomnicki L, et al. Microglia-derived TGF-beta as an important regulator of glioblastoma invasion—an inhibition of TGF-beta-dependent effects by shRNA against human TGF-beta type II receptor. *Oncogene.* 2008; 27(7):918-930.
20. Jacobs V L, Landry R P, Liu Y, Romero-Sandoval E A, and De Leo J A. Propentofylline decreases tumor growth in a rodent model of glioblastoma multiforme by a direct mechanism on microglia. *Neuro Oncol.* 2012; 14(2):119-131.
21. Squatrito M and Holland E C. DNA damage response and growth factor signaling pathways in gliomagenesis and therapeutic resistance. *Cancer Res.* 2011; 71(18): 5945-5949.
22. Maes W and Van Gool S W. Experimental immunotherapy for malignant glioma: lessons from two decades of research in the GL261 model. Cancer Immunol Immunother. 2011; 60(2):153-160.
23. Gabrusiewicz K, Ellert-Miklaszewska A, Lipko M, et al. Characteristics of the alternative phenotype of microglia/macrophages and its modulation in experimental gliomas. PLoS One. 2011; 6(8):e23902.
24. Zinser E, Turza N, and Steinkasserer A. CNI-1493 mediated suppression of dendritic cell activation in vitro and in vivo. Immunobiology. 2004; 209(1-2):89-97.
25. Lowenberg M, Verhaar A, van den Blink B, et al. Specific inhibition of c-Raf activity by semapimod induces clinical remission in severe Crohn's disease. J. Immunol. 2005; 175(4):2293-2300.
26. Cohen P S, Nakshatri H, Dennis J, et al. CNI-1493 inhibits monocyte/macrophage tumor necrosis factor by suppression of translation efficiency. Proc Natl Acad Sci USA. 1996; 93(9):3967-3971.
27. Ruffell B, Affara N I, and Coussens L M. Differential macrophage programming in the tumor microenvironment. Trends Immunol. 2012; 33 (3): 119-126.
28. Meng Y, Beckett M A, Liang H, et al. Blockade of tumor necrosis factor alpha signaling in tumor-associated macrophages as a radiosensitizing strategy. Cancer Res. 2010; 70(4):1534-1543.
29. DeNardo D G, Brennan D J, Rexhepaj E, et al. Leukocyte complexity predicts breast cancer survival and functionally regulates response to chemotherapy. Cancer Discov. 2011; 1(1):54-67.
30. Gursel D B, Berry N, and Boockvar J A. Therapeutic stem cells encapsulated in a synthetic extracellular matrix selectively kill tumor cells, delay tumor growth, and increase survival in a mouse resection model of malignant glioma. Neurosurgery. 2012; 70(6):N17-19.
31. Keunen O, Johansson M, Oudin A, et al. Anti-VEGF treatment reduces blood supply and increases tumor cell invasion in glioblastoma. Proc Natl Acad Sci USA. 2011; 108(9):3749-3754.
32. Lu K V, Chang J P, Parachoniak C A, et al. VEGF inhibits tumor cell invasion and mesenchymal transition through a MET/VEGFR2 complex. Cancer Cell. 2012; 22(1):21-35.
33. Atkins M B, Redman B, Mier J, et al. A phase I study of CNI-1493, an inhibitor of cytokine release, in combination with high-dose interleukin-2 in patients with renal cancer and melanoma. Clin Cancer Res. 2001; 7(3):486-492.
34. Hommes D, van den Blink B, Plasse T, et al Inhibition of stress-activated MAP kinases induces clinical improvement in moderate to severe Crohn's disease. Gastroenterology. 2002; 122(1):7-14.

What is claimed is:

1. A method of treating an astrocytoma in a subject, wherein the subject is also being treated with ionizing radiotherapy for the astrocytoma, comprising administering to the subject an amount of a guanylhydrazone compound having the formula:

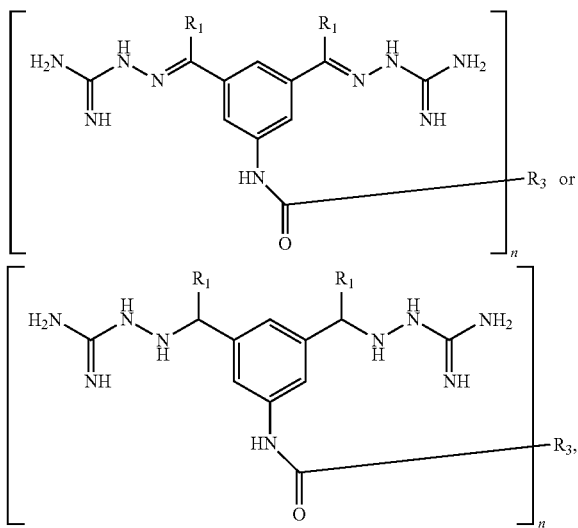

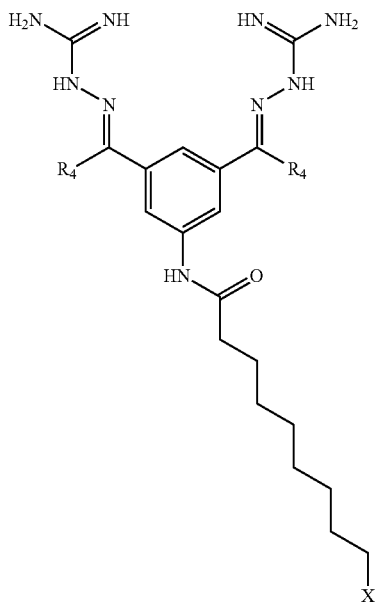

wherein in each case, n=1 or 2, and wherein when n=2, the two molecules are joined through $R_3$, wherein each $R_1$ is, independently, chosen from —H or —CH$_3$, and wherein $R_3$ is a C1-C10 hydrocarbyl, branched or unbranched, optionally substituted;

or having the formula:

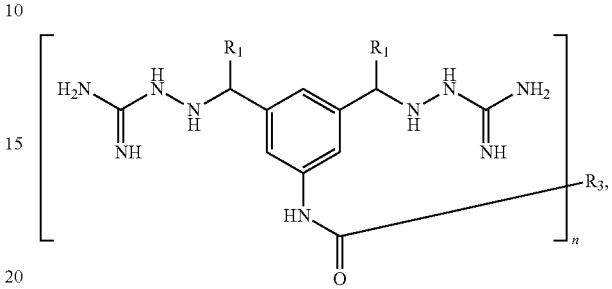

wherein each $R_4$ is, independently, chosen from —H or —CH$_3$, and wherein X=C2-C8 alkynyl, —CN$_3$, or —C(O)NHR wherein R is a di-substituted aryl, or is a pharmaceutically acceptable salt thereof, effective to treat an astrocytoma.

2. The method of claim 1, wherein the astrocytoma is a glioblastoma.

3. The method of claim 2, wherein glioblastoma is a glioblastoma multiforme.

4. The method of claim 1, wherein the guanylhydrazone compound has the formula:

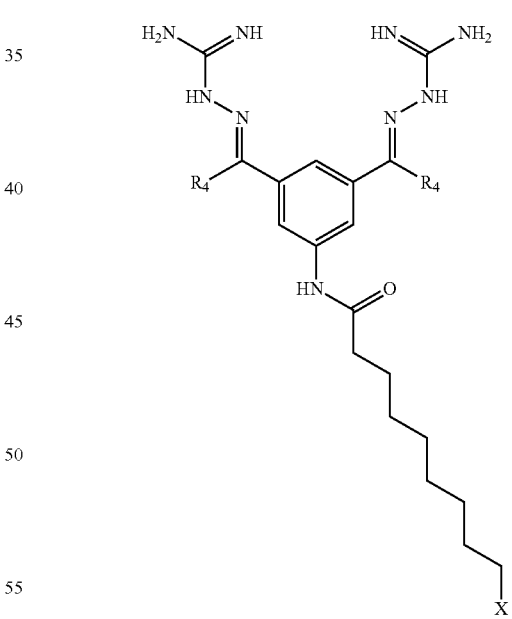

wherein n=1 or 2, and wherein when n=2, the two molecules are joined through $R_3$, wherein each $R_1$ is, independently, chosen from —H or —CH$_3$, and wherein $R_3$ is a C1-C10 hydrocarbyl, branched or unbranched, optionally substituted;

or wherein the guanylhydrazone compound has the formula:

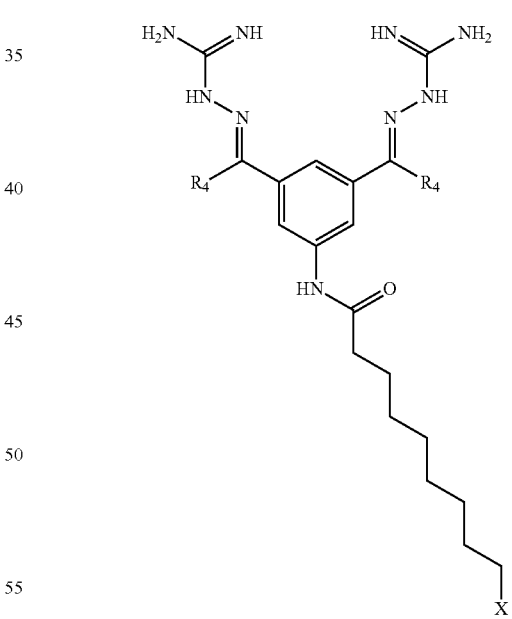

wherein each $R_4$ is, independently, chosen from —H or —CH$_3$, and wherein X=C2-C8 alkynyl, —CN$_3$, or —C(O)NHR wherein R is a di-substituted aryl, or is a pharmaceutically acceptable salt thereof.

5. The method of claim 1, wherein the guanylhydrazone compound has the structure:

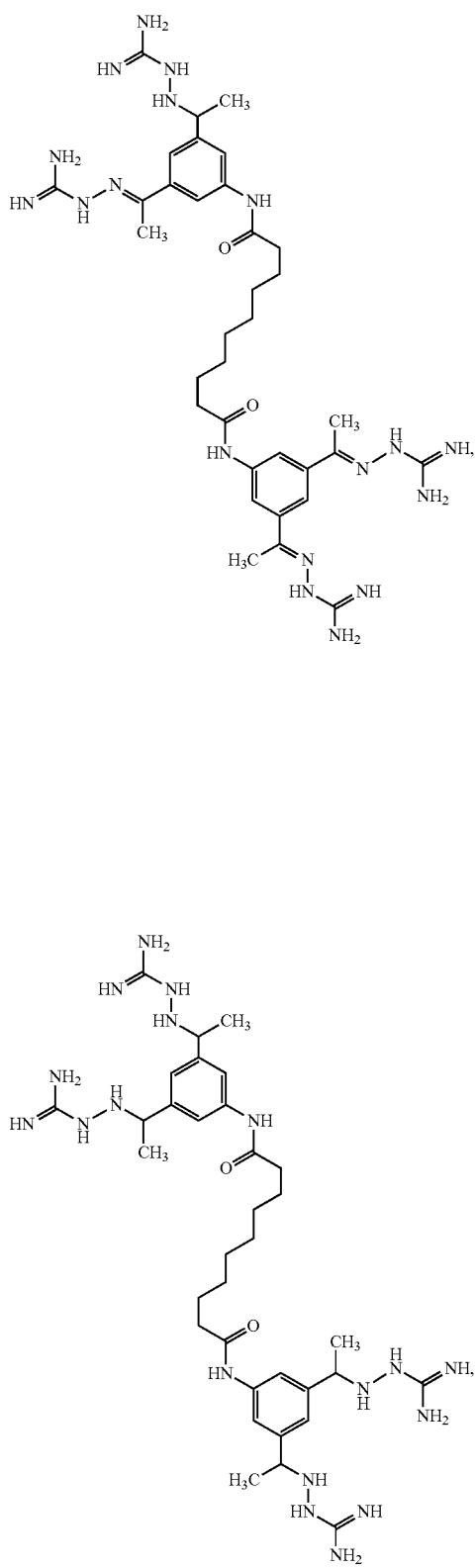 [SMILES: C/C(=N\NC(=N)N)c1cc(NC(=O)CCCCCCCCC(=O)Nc2cc(/C(C)=N/NC(=N)N)cc(C(C)NNC(=N)N)c2)cc(/C(C)=N/NC(=N)N)c1 ; CC(NNC(=N)N)c1cc(NC(=O)CCCCCCCCC(=O)Nc2cc(C(C)NNC(=N)N)cc(C(C)NNC(=N)N)c2)cc(C(C)NNC(=N)N)c1]

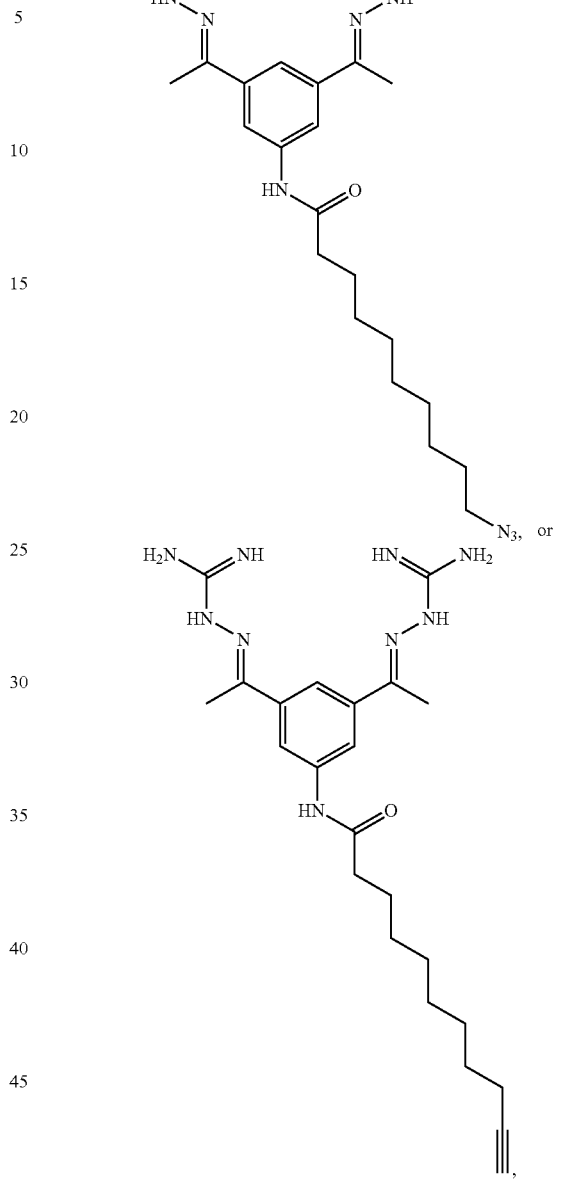

or is a pharmaceutically acceptable salt thereof.

6. The method of claim 1, wherein the guanylhydrazone compound is administered in a manner effective to deliver it to a brain of a subject.

7. The method of claim 1, wherein the guanylhydrazone compound is administered into the brain of the subject.

8. The method of claim 1, further comprising administering an anti-tumor therapy to the subject.

9. The method of claim 8, wherein the anti-tumor therapy comprises brain tumor radiation therapy.

* * * * *